United States Patent [19]
De Greef et al.

[11] Patent Number: 5,633,441
[45] Date of Patent: May 27, 1997

[54] PLANTS WITH GENETIC FEMALE STERILITY

[75] Inventors: Willy De Greef, Ghent; John Van Emmelo, Sint-Amandsberg, both of Belgium; Dulce E. De Oliveira, Rio de Janeiro, Brazil; Maria-Helena De Souza, Ghent; Marc Van Montagu, Brussels, both of Belgium

[73] Assignee: Plant Genetic Systems, N.V., Ghent, Belgium

[21] Appl. No.: 361,467

[22] Filed: Dec. 22, 1994

Related U.S. Application Data

[63] Continuation of Ser. No. 681,492, filed as PCT/EP90/01275 Aug. 1, 1990, abandoned.

[30] Foreign Application Priority Data

Aug. 4, 1989 [EP] European Pat. Off. ............. 89402224

[51] Int. Cl.$^6$ ............................. A01H 5/00; C12N 15/11; C12N 15/82
[52] U.S. Cl. .................... 800/205; 800/200; 536/24.1; 435/172.3; 435/418; 435/320.1; 435/419
[58] Field of Search ............................... 435/172.3, 240.4, 435/320.1; 536/24.1; 800/205, 200

[56] References Cited

U.S. PATENT DOCUMENTS

| | | | |
|---|---|---|---|
| 4,751,348 | 6/1988 | Malmberg et al. | 800/230 |
| 5,007,198 | 4/1991 | Gray et al. | 47/58 |
| 5,053,331 | 10/1991 | Clarke et al. | 435/172.3 |
| 5,066,830 | 11/1991 | Morrison et al. | 800/230 |

FOREIGN PATENT DOCUMENTS

| | | |
|---|---|---|
| 0198288 | 10/1986 | European Pat. Off. |
| 0329308 | 8/1989 | European Pat. Off. |
| 0344029 | 11/1989 | European Pat. Off. |
| 0343947 | 11/1989 | European Pat. Off. |

OTHER PUBLICATIONS

Thorsness et al 1991 Developmental Biology 143:173–184.
Klee et al., *Journal of Cellular Biochemistry*, 12C: L051 (Apr. 1988).
R. Bernatzky et al., "A Nuclear Sequence Associated with Self–Incompatibility in *Nicotiana alata* has homology with mitochondrial DNA", *Theor. Appl. Genet.*, vol. 77:320–324 (1989).
Gasser et al., "Isolation of Tissue–Specific cDNAs from Tomato Pistils", *The Plant Cell*, vol. 1:15–24, Jan. 1989.
Twell et al., "Pollen–Specific Expression directed by Chimeric Genes in Transgenic Tomato and Tobacco Plants", *Journal of Cellular Biochemistry*, 13D: M349 (Apr. 1989).
Medford et al., "Alterations of Endogenous Cytokinins in Transgenic Plants Using a Chimeric IsopentenylTransferase Gene", *The Plant Cell*, vol. 1:403–413, Apr. 1989.
Benfey et al., "Regulated Genes in Transgenic Plants", *Science*, vol. 244:174–181. (14 Apr. 89).
T. Schmülling, et al., "Single genes from *Agrobacterium rhizogenes* influence plant development", *The EMBO Journal*, vol. 7, No. 9:2621–2629, 1988.

*Primary Examiner*—Patricia R. Moody
*Attorney, Agent, or Firm*—Burns, Doane, Swecker & Mathis, L.L.P.

[57] ABSTRACT

The invention concerns female-sterile plants that comprise a foreign DNA incorporated in the nuclear genome of their cells. This foreign DNA first comprises a female-sterility DNA encoding a protein or polypeptide such as barnase which, when produced in the cells of the plant, kills or significantly disturbs the metabolism, functioning or development of the cells. The foreign DNA also comprises a first promoter which directs expression of the female-sterility DNA selectively in style cells, stigma cells or style-and stigma cells of the female reproductive organs of the plants. The first promoter does not direct detectable expression of the female sterility DNA in the ovule or in other parts of the plant so that the plant remains male-fertile. The female-sterility DNA is in the same transcriptional unit as and under the control of the first promoter.

43 Claims, 19 Drawing Sheets

```
                   9                  18                 27                 36
        GAA TTC CCA TTG CCT TTC GAA TTG CCA CCA GCG GAG ATC
        Glu Phe Pro Leu Pro Phe Glu Leu Pro Pro Ala Glu Ile 45                 54                 63                 72
        CCA TTG CCG GAG ATC CCA TTG CCT TTC GAT GGG CCT ACA
        Pro Leu Pro Glu Ile Pro Leu Pro Phe Asp Gly Pro Thr 81                  90                 99                108                117
        TTC GTG CTA CCG CCA CCA TCA CCA CCA CCA CCT CCA TCG
        Phe Val Leu Pro Pro Pro Ser Pro Pro Pro Pro Pro Ser 126                135                144                153
        TCA CCA TCT CCA TCT CCA GCA AAG CAA TCA CCA CCA CCT
        Ser Pro Ser Pro Ser Pro Ala Lys Gln Ser Pro Pro Pro 162                171                180                189
        CCT CGG GCA CCA TCA CCA TCA CCA GCT ACT CAG CCA CCT
        Pro Arg Ala Pro Ser Pro Ser Pro Ala Thr Gln Pro Pro 198                207                216                225                234
        ATA AAG CAA CCG CCA CCA CCA AGT GCT AAG AAA TCT CCT
        Ile Lys Gln Pro Pro Pro Ser Ala Lys Lys Ser Pro 243                252                261                270
        CCG CCA CCA GTT GCT TAT CCA CCA GTT ATG GCA CCA TCT
        Pro Pro Pro Val Ala Tyr Pro Pro Val MET Ala Pro Ser 279                288                297                306
        CCA TCA CCG GCT GCT GAG CCA CCT ATT ATA GCA CCA TTT
        Pro Ser Pro Ala Ala Glu Pro Pro Ile Ile Ala Pro Phe
```

FIG. 1A-1

```
 315          324         333         342         351
 CCA TCA CCA ACA GCG AAT CTA CCC CTT ATT CCC CGT CGA
 Pro Ser Pro Thr Ala Asn Leu Pro Leu Ile Pro Arg Arg 360         369         378         387
 CCA GCA CCA CCA GTA GTT AAG CCG CTT CCA CCT TTG GGG
 Pro Ala Pro Pro Val Val Lys Pro Leu Pro Pro Leu Gly 396         405         414         423
 AAG CCC CCT ATC GTC AAT GGC CTT GTT TAT TGT AAA TCC
 Lys Pro Pro Ile Val Asn Gly Leu Val Tyr Cys Lys Ser 432         441         450         459         468
 TGC AAC AGC TAT GGG TTC CCC ACT CTG CTC AAC ACC TCC
 Cys Asn Ser Tyr Gly Phe Pro Thr Leu Leu Asn Thr Ser 477         486         495         504
 CTA CTC CCA GGA GCT GTT GTG AAA CTA GTT TGC TAC AAC
 Leu Leu Pro Gly Ala Val Val Lys Leu Val Cys Tyr Asn 513         522         531         540
 GGA AAG AAA ACA ATG GTT CAA TCG GCG ACG ACA GAC AAC
 Gly Lys Lys Thr MET Val Gln Ser Ala Thr Thr Asp Asn 549         558         567         576         585
 AAA GGT GAG TTT CGG ATC ATT CCC AAA TCA TTA ACC AGA
 Lys Gly Glu Phe Arg Ile Ile Pro Lys Ser Leu Thr Arg 594         603         612         621
 GCA GAT GTT GGC AAG TGC AAG TTA TAT TTA GTG AAA TCA
 Ala Asp Val Gly Lys Cys Lys Leu Tyr Leu Val Lys Ser
```

FIG. 1A-2

```
     630         639         648         657
CCA AAT CCA AAT TGC AAT GTC CCA ACA AAT TTC AAT GGT
Pro Asn Pro Asn Cys Asn Val Pro Thr Asn Phe Asn Gly 666         675         684         693         702
GGA AAA TCT GGT GGT TTA TTG AAG CCT CTC CTA CCA CCT
Gly Lys Ser Gly Gly Leu Leu Lys Pro Leu Leu Pro Pro 711         720         729         738
AAA CAA CCG ATT ACC CCT GCC GCT GTC CCT CTA TCT GAT
Lys Gln Pro Ile Thr Pro Ala Ala Val Pro Leu Ser Asp 747         756         765         774
TTA TAT GGT GTT GGA CCT TTT ATA TTT GAA GCC TCC AGC
Leu Tyr Gly Val Gly Pro Phe Ile Phe Glu Ala Ser Ser 783         792         801         810         819
AAA ATG CCA TGC GAT AAG AAT TGA GCT CCT CAT TAC TAG
Lys MET Pro Cys Asp Lys Asn  .  Ala Pro His Tyr  .

828         837         846         855
AGC GAT AAT GTA TAA GAG CAT GAG TTT GTG ACG GAA ATT
Ser Asp Asn Val  .  Glu His Glu Phe Val Thr Glu Ile 864         873         882         891
ATT TTT TTC TTT TTT GTT CTA TAG TTT ATA CAA GGA GAC
Ile Phe Phe Phe Phe Val Leu  .  Phe Ile Gln Gly Asp 900         909         918         927         936
AGA AAA CTT TGT ATC ACT ATA CAG AAA TCA AAT GAG TCG
Arg Lys Leu Cys Ile Thr Ile Gln Lys Ser Asn Glu Ser
```

FIG. 1A-3

```
         945             954             963
CAA AAG TCA AAA TCG AAT TTA TGA AAA
Gln Lys Ser Lys Ser Asn Leu  .  Lys
```

FIG. 1A-4

```
              11              20              29              38
     GA ATT CCG GCT TTT ACA TCA GTA AAG ATC CTA GTG CTC
        Ile Pro Ala Phe Thr Ser Val Lys Ile Leu Val Leu 47              56              65              74
     ATA CAA GTT TCA GTT TTA GCA CTC AGC TCA TTC TCA GAG
     Ile Gln Val Ser Val Leu Ala Leu Ser Ser Phe Ser Glu 83              92             101             110
     CTT AGC TTT GGT AAA GGA ATT GAA AGC TCG TCA TTA GAC
     Leu Ser Phe Gly Lys Gly Ile Glu Ser Ser Ser Leu Asp 119             128             137             146             155
     AAA GGA CAA CAC CAT CCA ATC TTC TCA ACA GTT CAC TTA
     Lys Gly Gln His His Pro Ile Phe Ser Thr Val His Leu 164             173             182             191
     TTC TTT GGA AAG TCT CCC AAG AAA AGC CCC TCT AGC CCT
     Phe Phe Gly Lys Ser Pro Lys Lys Ser Pro Ser Ser Pro 200             209             218             227
     ACA CCG GTA AAC AAG CCA TCA CCA TCA CCA CCA CCA CAG
     Thr Pro Val Asn Lys Pro Ser Pro Ser Pro Pro Pro Gln 236             245             254             263             272
     GTT AAG TCA TCC CTT CCG CCG CCT GCT AAG TCA CCA CCG
     Val Lys Ser Ser Leu Pro Pro Pro Ala Lys Ser Pro Pro 281             290             299             308
     CCG CCA CCA GCT AAG TCA CCA CCT CCT CTG CTG CCT CCA
     Pro Pro Pro Ala Lys Ser Pro Pro Pro Leu Leu Pro Pro
```

FIG. 1B-1

```
      317           326           335           344
CCA CCA TCT CAA CCA CCA AAA CAA CCA CCT CCA CCT CCG
Pro Pro Ser Gln Pro Pro Lys Gln Pro Pro Pro Pro Pro 353           362           371           380           389
CCG CCA CCA GCA AAG CAA CCA CCA TCT GCT AAG CCA CCT
Pro Pro Pro Ala Lys Gln Pro Pro Ser Ala Lys Pro Pro 398           407           416           425
ATT AAA CCT CCA TCT CCG TCA CCG GCT GCT CAG CCA CCA
Ile Lys Pro Pro Ser Pro Ser Pro Ala Ala Gln Pro Pro 434           443           452           461
GCA ACG CAA CGA GCA ACA CCA CCA CCG GCA ATG CAA CGG
Ala Thr Gln Arg Ala Thr Pro Pro Pro Ala MET Gln Arg

470
GCA CC
Ala
```

FIG. 1B-2

```
                9              18              27              36
         GCC CTG TAG CGG CAT TAA GCG CGG CGG GTG TGG TGG TTA
         Ala Leu  .  Arg His  .  Ala Arg Arg Val Trp Trp Leu 45              54              63              72
         CGC GCA GTG ACC GCT ACA CTT GCC AGC GCC CTA GCG CCC
         Arg Ala Val Thr Ala Thr Leu Ala Ser Ala Leu Ala Pro 81              90              99             108             117
         GCT CCT TTC GCT CTT CTC ATT CTC ATC ATC CTC ACT CTT
         Ala Pro Phe Ala Leu Leu Ile Leu Ile Ile Leu Thr Leu 126             135             144             153
         TCT AGC ACA CCA ATT ACC ACA ATG TCT ATA CCC GAG ACA
         Ser Ser Thr Pro Ile Thr Thr MET Ser Ile Pro Glu Thr 162             171             180             189
         AAC CGT AGA AAT GCA ACT ACA AAC TCT TAC ACC GAT GTT
         Asn Arg Arg Asn Ala Thr Thr Asn Ser Tyr Thr Asp Val 198             207             216             225             234
         GCT CTT TCT GCG CGA AAA GGT GCA TTT CCT CCT CCC AGA
         Ala Leu Ser Ala Arg Lys Gly Ala Phe Pro Pro Pro Arg 243             252             261             270
         AAG CTA GGA GAA TAC TCG ACA AAT TCT ACC GAC TAC AAC
         Lys Leu Gly Glu Tyr Ser Thr Asn Ser Thr Asp Tyr Asn 279             288             297             306
         TTG ATC TGC AAA ACT TGC AAG AGA TTA TCG GAA CGC AAT
         Leu Ile Cys Lys Thr Cys Lys Arg Leu Ser Glu Arg Asn
```

FIG. 2A-1

```
315             324             333             342             351
ACA TGT TGT TTC AAC TAC AGT TGT GTT GAT GTG TCC ACC
Thr Cys Cys Phe Asn Tyr Ser Cys Val Asp Val Ser Thr 360             369             378             387
AAC AGG TTC AAC TGT GGC TCC TGT GGC CTT GTC TGT AAC
Asn Arg Phe Asn Cys Gly Ser Cys Gly Leu Val Cys Asn 396             405             414             423
CTT GGA ACG AGA TGC TGT GGT GGG ATC TGT GTG GAC ATC
Leu Gly Thr Arg Cys Cys Gly Gly Ile Cys Val Asp Ile 432             441             450             459             468
CAG AAA GAC AAT GGC AAT TGT GGC AAG TGT TCT AAT GTT
Gln Lys Asp Asn Gly Asn Cys Gly Lys Cys Ser Asn Val 477             486             495             504
TGC TCT CCT GGT CAG AAG TGT TCA TTT GGG TTT TGT GAC
Cys Ser Pro Gly Gln Lys Cys Ser Phe Gly Phe Cys Asp 513             522             531             540
TAT GCC TAA GTA TAT TTT CCC TAT GTC TAG TAA TAA CCA
Tyr Ala  .  Val Tyr Phe Pro Tyr Val  .   .   .  Pro 549             558             567             576             585
GAG TCT GTG TAA GCC TGT CAA ATA ACT AAC TCC CCT GTC
Glu Ser Val  .  Ala Cys Gln Ile Thr Asn Ser Pro Val 594             603             612             621
CCT AGG GTG AAA TGT TAC TCT AAT AAC GTT GGA GAT TTG
Pro Arg Val Lys Cys Tyr Ser Asn Asn Val Gly Asp Leu
```

FIG. 2A-2

```
 630            639            648            657
CAT TCT GTG TTG TTT GTA GTA AGT TAT GGC TAG TAA TCT
His Ser Val Leu Phe Val Val Ser Tyr Gly  .   .  Ser 666            675            684            693            702
ATT TAA GGT GAC TTG GAA TAC ATA AAA AAA AAA AAA AAA
Ile  .  Gly Asp Leu Glu Tyr Ile Lys Lys Lys Lys Lys 711            720            729            738
AAA AAA AAA AAA AAA AAA AAA AAA AAA AAA AAA AAA AAA
Lys Lys Lys Lys Lys Lys Lys Lys Lys Lys Lys Lys Lys

747
AAA TGC A
Lys Cys
```

FIG. 2A-3

```
                    11           20           29          38
         CC CTT GTT CTT TTT CAG CTT TCA GTT TTA TTA CTT AGC
            Leu Val Leu Phe Gln Leu Ser Val Leu Leu Leu Ser 47           56           65           74
         TCA TTC ACA GTA GTT CTT AGC CAG GAG GAA GAC ATT GGG
         Ser Phe Thr Val Val Leu Ser Gln Glu Glu Asp Ile Gly 83           92          101          110
         GGT TGG TTT ACC ACC AAA CAT CAT GAC CAC CTT TCA CCA
         Gly Trp Phe Thr Thr Lys His His Asp His Leu Ser Pro 119          128          137          146         155
         GCT CAA GCT CCT AAG CCT CAC AAA GGC CAC CAC CAC CCC
         Ala Gln Ala Pro Lys Pro His Lys Gly His His His Pro 164          173          182          191
         AAA CAT TCC CCA GCC CCT TCA CCA ACT AAG CCT CCC ACT
         Lys His Ser Pro Ala Pro Ser Pro Thr Lys Pro Pro Thr 200          209          218          227
         TAT AGC CCA TCG AAA CCA CCA GTT AAA CCA CCG GTT AAA
         Tyr Ser Pro Ser Lys Pro Pro Val Lys Pro Pro Val Lys 236          245          254          263         272
         CCA CCA ACT AAG GCT CCC ACT TAT AGC CCA TCA AAA CCA
         Pro Pro Thr Lys Ala Pro Thr Tyr Ser Pro Ser Lys Pro 281          290          299          308
         CCA GCT AAG CCA CCA GTT AAA CCA CCA ACA CCA ACA CCA
         Pro Ala Lys Pro Pro Val Lys Pro Pro Thr Pro Thr Pro
```

FIG. 2B-1

```
        317             326             335             344
TCA CCT TAT CCT GCT CCT GCT CCT ATT ACT AGG AAA CCT
Ser Pro Tyr Pro Ala Pro Ala Pro Ile Thr Arg Lys Pro 353             362             371             380             389
GTA GCA GTC CGT GGC CTT GTT TAC TGC AAG CCG TGC AAG
Val Ala Val Arg Gly Leu Val Tyr Cys Lys Pro Cys Lys 398             407             416             425
TTT AGA GGG GTT AAA ACT CTA AAC CAA GCT TCC CCA CTC
Phe Arg Gly Val Lys Thr Leu Asn Gln Ala Ser Pro Leu 434             443             452             461
CTG GGT GCG GTA GTG AAG CTA GTA TGC AAC AAC ACA AAG
Leu Gly Ala Val Val Lys Leu Val Cys Asn Asn Thr Lys 470             479             488             497             506
AAG ACA TTA GTG GAA CAG GGC AAG ACA GAC AAG AAT GGC
Lys Thr Leu Val Glu Gln Gly Lys Thr Asp Lys Asn Gly 515             524             533             542
TTC TTC TGG ATC ATG CCC AAA TTC TTG TCC TCA GCA GCT
Phe Phe Trp Ile MET Pro Lys Phe Leu Ser Ser Ala Ala 551             560             569             578
TAC CAC AAA TGC AAG GTG TTC TTG GTC TCA TCA AAC AAT
Tyr His Lys Cys Lys Val Phe Leu Val Ser Ser Asn Asn 587             596             605             614             623
ACT TAC TGT GAT GTC CCA ACA GAT TAC AAT GGT GGA AAA
Thr Tyr Cys Asp Val Pro Thr Asp Tyr Asn Gly Gly Lys
```

FIG. 2B-2

```
            632            641            650            659
TCT GGT GCT TTG TTG AAA TAC ACC CCA CTT CCT AAG CCA
Ser Gly Ala Leu Leu Lys Tyr Thr Pro Leu Pro Lys Pro 668            677            686            695
CCA GCA GCT ACT TCT CTC CCT GTT AAA CTC CCC ACA TTT
Pro Ala Ala Thr Ser Leu Pro Val Lys Leu Pro Thr Phe 704            713            722            731            740
GAT GTC TTC ACT GTT GGA CCT TTT GGT TTC GAA CCC TCA
Asp Val Phe Thr Val Gly Pro Phe Gly Phe Glu Pro Ser 749            758            767            776
AAG AAG GTG CCA TGC AAA AAG TAA CTT GCA TGG GAA ATT
Lys Lys Val Pro Cys Lys Lys  .  Leu Ala Trp Glu Ile 785            794            803            812
AGA AAG ATA GGA AGG AAA AAT TAA TTA TGT GTT GAA GAA
Arg Lys Ile Gly Arg Lys Asn  .  Leu Cys Val Glu Glu 821            830            839            848            857
AGA CGA TTA TGT ACC TGT TTC CTG TGT TCT TGT TAT TAT
Arg Arg Leu Cys Thr Cys Phe Leu Cys Ser Cys Tyr Tyr 866            875            884            893
TTT ATT AAT AAA TGA AGC AAA GAG GAA AGA ACG TAG TTT
Phe Ile Asn Lys  .  Ser Lys Glu Glu Arg Thr  .  Phe 902            911            920            929
TCT TGT TTT CCT ATT TTG TTT CTC TCT ATC AAA ACC CAA
Ser Cys Phe Pro Ile Leu Phe Leu Ser Ile Lys Thr Gln
```

FIG. 2B-3

```
938         947         956         965         974
CAA GTA AAA TGG ATT TAT AAG TTT TTC TTC AAA AAA AAA
Gln Val Lys Trp Ile Tyr Lys Phe Phe Phe Lys Lys Lys 983         992         1001        1010
AAA AAA AAA AAA AAA AAA AAA AAA AAA AAA AAA AAA AAA
Lys Lys Lys Lys Lys Lys Lys Lys Lys Lys Lys Lys Lys 1019        1028        1037        1046
AAA AAA AAA AAA AAA AAA AAA AAT GCA GGT CGA
Lys Lys Lys Lys Lys Lys Lys Asn Ala Gly Arg
```

FIG. 2B-4

PLANTS WITH GENETIC FEMALE STERILITY

This application is a continuation of application Ser. No. 07/681,492, filed as PCT/EP90/01275 Aug. 1, 1990 (now abandoned).

This invention relates to a female-sterile plant and to its reproductive material (e.g., seeds), in which the cells have been transformed so that a foreign DNA sequence is stably integrated into their nuclear genome. The foreign DNA sequence of this invention contains a first foreign DNA (hereinafter the "female-sterility DNA") that: 1) encodes a first RNA, protein or polypeptide which, when produced or overproduced in a cell of a flower, particularly a female organ thereof, or a seed or an embryo of a plants disturbs significantly the metabolism, functioning and/or development of the cell of the flower or seed or embryo; and 2) is in the same transcriptional unit as, and under the control of, a first promoter which is capable of directing expression of the female-sterility DNA selectively in cells of the flowers, particularly one or more of their female organs, or seeds or embryos of the plant. In particular, this invention relates to such a nuclear female-sterile plant and its reproductive material, in which the foreign DNA sequence of this invention is a foreign chimaeric DNA sequence that can also contain a second foreign DNA (the "marker DNA") that: encodes a second RNA, protein or polypeptide which, when present at least in a specific tissue or specific cells of the plant, renders the entire plant easily separable from other plants that do not contain the second RNA, protein or polypeptide at least in the specific tissue or specific cells; 2) is in the same transcriptional unit as, and under the control of, a second promoter which is capable of directing expression of the marker DNA in at least the specific tissue or the specific cells of the plant; and 3) is in the same genetic locus of the nuclear genome of the cells of the plant as the female-sterility DNA.

This invention also relates to a foreign chimaeric DNA sequence that contains at least one female-sterility DNA under the control of at least one first promoter and that can also contain, adjacent to the female-sterility DNA(s) and the first promoter(s), at least one marker DNA under the control of at least one second promoter.

This invention further relates to a vector that contains the foreign DNA sequence of this invention and is suitable for the transformation of a plant cell, whereby the foreign DNA sequence is stably integrated into the nuclear genome of the cell.

This invention still further relates to cells of a plant and to plant cell cultures, the nuclear genomes of which are transformed with the foreign DNA sequence.

This invention yet further relates to a process for producing a nuclear female-sterile male-fertile plant and its reproductive material containing the foreign DNA sequence in which the female-sterility DNA: 1) is under the control of the first promoter; 2) is stably integrated into the nuclear genome of the plant's cells; 3) can be expressed selectively in cells of each flower, particularly a female organ thereof, or each seed or each embryo of the plant in the form of the first RNA, protein or polypeptide; and optionally 4) is in the same genetic locus as the marker DNA under the control of the second promoter.

The invention further relates to a process for producing hybrid seeds, which grow into hybrid plants, by crossing: 1) the female-sterile plant of this invention which may include, in its nuclear genome, the marker DNA, preferably encoding a protein conferring a resistance to a herbicide on the plant; and 2) a female-fertile plant without the marker DNA in its genome. This invention particularly relates to such a process for producing hybrid seeds on a commercial scale, preferably in a substantially random population, without the need for extensive hand-labor.

BACKGROUND OF THE INVENTION

Hybridization of plants is recognized as an important process for producing offspring having a combination of the desirable traits of the parent plants. The resulting hybrid offspring often has the ability to outperform the parents in different traits, such as in yield, adaptability to environmental changes, and disease resistance. This ability is called "heterosis" or "hybrid vigor". As a result, hybridization bas been used extensively for improving major crops, such as corn, sugar beet and sunflower. For a number of reasons, primarily related to the fact that most plants are capable of undergoing both self-pollination and cross-pollination, the controlled cross-pollination of plants without significant self-pollination, to produce a harvest of hybrid seeds, has been difficult to achieve on a commercial scale.

In nature, the vast majority of crop plants produce male and female reproductive organs on the same plant, usually in close proximity to one another in the same flower. This favors self-pollination. Some plants, however, are exceptions as a result of the particular morphology of their reproductive organs which favors cross-pollination. These plants produce hybrid offspring with improved vigor and adaptability. One such morphology in *Cannabis ssp.* (hemp) involves male and female reproductive organs on separate plants. Another such morphology in *Zea mays* (corn) involves male and female reproductive organs on different parts of the same plant. Another such morphology in *Elaeis guineensis* (oil palm) involves male and fertile female gametes which become fertile at different times in the plant's development.

Some other plant species, such as *Ananas comosus* (pineapple), favor cross-pollination through the particular physiology of their reproductive organs. Such plants have developed a so-called "self-incompatibility system" whereby the pollen of one plant is not able to fertilize the female gamete of the same plant or of another plant with the same genotype.

Some other plant species favor cross-pollination by naturally displaying the so-called genomic characteristic of "male sterility". By this characteristic, the plants' anthers degenerate before pollen, produced by the anthers, reaches maturity. See: "Male-Sterility in Higher Plants", M. L. B. Kaul, 1987, in: Monographs on Theoretical and Applied Genetics 10, Edit. Springer Verlag. Such a natural male-sterility characteristic is believed to result from a wide range of natural mutations, most often involving recessive deficiencies, and this characteristic can not easily be maintained in plant species that predominantly self-pollinate, since under natural conditions, no seeds will be produced.

Some other plants favor cross-pollination by natually displaying the character of "female-sterility" due to a deficient functioning of either the female gametophyte, the female gamete, the female zygote, or the seed. These plants produce no viable seeds. There are many different mutations that can lead to this condition, involving all stages of development of a specific tissue of the female reproductive organ. This characteristic distinguishes female-sterility from the more widely known phenomena of male-sterility and self-incompatibility. Although reducing the number of offspring a species can produce, the female-sterility trait has some evolutionary advantages in nature for some plants, especially for perennials. In perennials, the rate of vegetative growth is to a large extend determined by the distribution of biomass between vegetative and reproductive plant tissues. Female-sterile plants therefore tend to grow more vigorously than the female-fertile plants.

Although female-sterility inducing mutations probably occur as frequently as male-sterility inducing mutations, female-sterility inducing mutations are much less used in plant breeding and seed production and consequently much less studied, and only few examples of such mutations exist.

A well documented illustration of natural female-sterility is the oil palm (*Elaeis guineensis*) where the so-called "pisifera" condition is characterized by the inability of the developing seed to produce a shell. As a result, the developing seed aborts in an early stage, and no ripe fruit is formed. The gene encoding the "pisifera" genotype acts as a semi-dominant allele. Plants homozygous for the allele are not capable of producing a seed shell and consequently no ripe fruit or seeds. Plants heterozygotic for the allele produce ripe fruit and seeds with a thin shell (0.5 to 2 mm), while wild-type plants (which do not carry the allele) produce ripe fruit and seeds with shells of 2 to 6 mm thickness. These two genotypes are indistinguishable in seed yield, and their genotype is determined by that of the female parent plant. In oil palm breeding, the "pisifera" type is used as the male parent plant in all commercial seed production. By crossing pollen from the "pisifera" palms with the wild-type female parent plants, a homogeneous F1 hybrid seed population, producing thin-shelled fruit, is obtained.

Another example of a plant with a natural female-sterility, used for the commercial production of hybrid seed; is alfalfa. Alfalfa was known to have male-sterility genes, but in testing a hybrid seed production system in which male-sterile and male fertile plants were sown in separate bands, it appeared that a negligeable amount of hybrid seeds was produced. This low production was due to the fact that honeybees, responsible for pollination, have low affinity for male-sterile plants, favoring the self-pollination of the male-fertile plants. To obtain good seed set, it seemed necessary to interplant very closely to each other (thus not in separate rows) the male-fertile and the male-sterile parent plants. This was made possible when a female-sterility gene was discovered and bred into the male-fertile plants. Consequently, the only seeds which could be produced in the randomly sown plots were hybrid seeds obtained by cross-pollination between the female-sterile and the male-sterile parent plants.

For other crops, female-sterility has been reported, such as sorghum (Casady et al (1960) J. Hered. 51, 35–38), cotton (Tustus and Meyer (1963) J. Hered. 54, 167–168), tomato (Honma and Pratak (1964) J. Hered. 55, 143–145), wheat (Gotzov and Dzelepov (1974) Gen. Plant Breed. 7, 480–487), and pearl millet (Hanna and Powel (1974) J. Hered. 65, 247–249). There are, however, several problems in maintaining the female-sterile lines, and for this reason, such lines are not used on a commercially important scale.

Compared with male-sterility, the use of female-sterility offers some other advantages in the production of hybrid seeds. Female-sterility allows the production of fruits without seeds and enhanced vegetative biomass production and can, in some cases, induce more flower-setting within one season.

SUMMARY OF THE INVENTION

In accordance with this invention, a cell of a plant is provided, in which the nuclear genome contains, stably integrated therein, a foreign DNA sequence, preferably a foreign chimaeric DNA sequence, characterized by:

(a) a female-sterility DNA encoding a first RNA, protein or polypeptide which, when produced or overproduced in a cell of a flower, particularly a female organ thereof, a seed or an embryo of the plant, disturbs significantly the metabolism, functioning and/or development of the cell of the flower or seed or embryo; and (b) a first promoter capable of directing expression of the female-sterility DNA selectively in cells of the flowers, particularly a female organ thereof, seeds or embryos of the plant; the female-sterility DNA being in the same transcriptional unit as, and under the control of, the first promoter.

The foreign DNA sequence in the nuclear genome of the transformed cell can also comprise, preferably in the same genetic locus as the female-sterility DNA:

(c) a marker DNA encoding a second RNA, protein or polypeptide which, when present at least in a specific tissue or specific cells of the plant, renders the plant easily separable from other plants which do not contain the second RNA, protein or polypeptide at least in the specific tissue or specific cells; and (d) a second promoter capable of directing expression of the marker DNA at least in the specific tissue or specific cells; the marker DNA being in the same transcriptional unit as, and under the control of, the second promoter.

Also in accordance with this invention is provided a foreign chimaeric DNA sequence that comprises the female-sterility DNA and the first promoter and that can also comprise the marker DNA and the second promoter, as well as at least one additional DNA encoding: a transit peptide capable of transporting the first protein or polypeptide and/or the second protein or polypeptide into a chloroplast or mitochondria of a plant cell, in which the foreign chimaeric DNA sequence is expressed in its cytoplasm; and/or a secretory signal peptide capable of secreting the first protein or polypeptide and/or the second protein or polypeptide out of a plant cell or plant tissue, in which the foreign chimaeric DNA sequence is expressed.

Further in accordance with this invention are provided: a female-sterile male-fertile plant and a plant cell culture, each consisting of cells containing the foreign DNA sequence; a fruit of a female-sterile plant; hybrid seeds and plants produced by crossing the female-sterile plant with a female-fertile plant; and a process for producing such hybrid seeds, as well as seedless fruit.

Yet further in accordance with this invention are provided style-, stigma-, ovary-, seed- and embryo-specific first promoters.

BRIEF DESCRIPTION OF THE DRAWINGS

FIG. 1A shows the DNA sequences (SEQ ID No. 1) of the STMGO7 gene of Example 1.

FIG. 1B shows the cDNA sequence (SEQ ID No. 2) of the STMG08 gene of example 1.

FIG. 2A shows the cDNA sequence (SEQ ID No. 3) of the STMG4B12 gene of Example 1.

FIG. 2B shows the cDNA sequence (SEQ ID No. 4) of the STMG3C9 gene of Example 1.

DETAILED DESCRIPTION OF THE INVENTION

Figure 3:
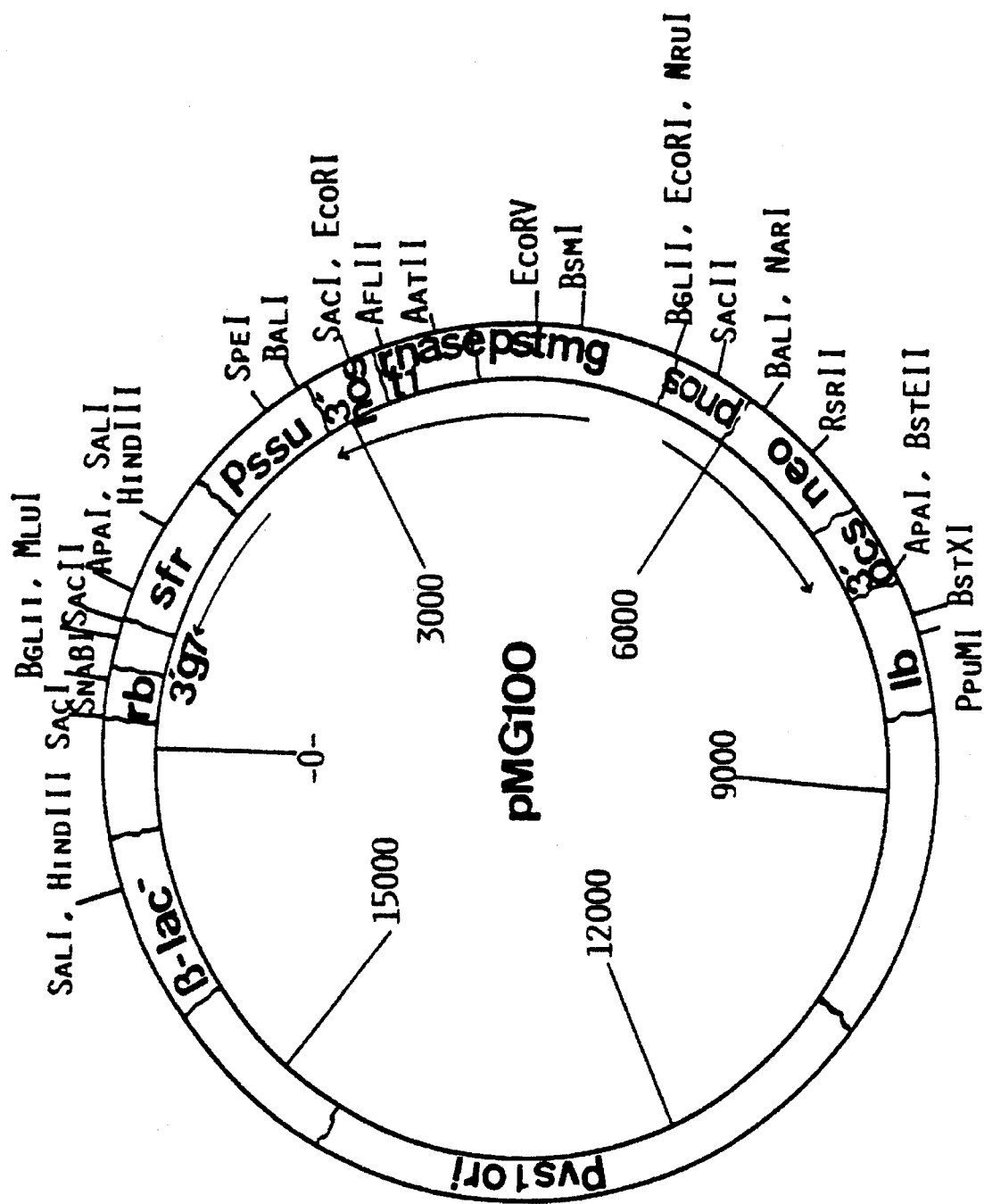
FIG. 3 shows a map of the vector pMG100 of Example 4.

In accordance with this invention, a female-sterile male-fertile plant is produced from a single cell of a plant by transforming the plant cell in a well known manner to stably insert, into the nuclear genome of the cell, the foreign DNA sequence of this invention. The foreign DNA sequence comprises at least one female-sterility DNA that is under the control of, and fused at its 5' end to, the first promoter and is fused at its 3' end to suitable transcription termination (or regulation) signals, including a polyadenylation signal. Thereby, the first RNA, protein or polypeptide is produced or overproduced selectively in cells of all the flowers, particularly in one or more female organs thereof, and/or in all the seeds and/or in all the embryos of the plant so as to render the plant female-sterile. The foreign DNA sequence can also comprise at least one marker DNA that is under the control of, and is fused at its 5' end to, the second promoter and is fused at its 3' end to suitable transcription termination signals, including a polyadenylation signal. The marker DNA is preferably in the same genetic locus as the female-sterility DNA, whereby the second RNA, protein or polypeptide is produced in at least the specific tissue or specific cells of the female-sterile plant so that the plant can be easily distinguished and/or separated from other plants that do not contain the second RNA, protein or polypeptide in the specific tissue or specific cells. This guarantees, with a high degree of certainty, the joint segregation of both the female-sterility DNA and the marker DNA into offspring of the plant.

The cell of the plant (particularly a plant capable of being infected with Agrobacterium) is preferably transformed in accordance with this invention, using a vector that is a disarmed Ti-plasmid containing the foreign DNA sequence and carried by Agrobacterium. This transformation can be carried out using procedures described, for example, in European patent publications 0,116,718 and 0,270,822. Preferred Ti-plasmid vectors contain the foreign DNA sequence between the border sequences, or at least located to the left of the right border sequence, of the T-DNA of the Ti-plasmid. Of course, other types of vectors can be used to transform the plant cell, using procedures such as direct gene transfer (as described, for example, in European patent publication 0,223,247), pollen mediated transformation (as described, for example, in European patent publication 0,270,356, PCT publication WO85/01856, and European patent publication 0,275,069), in vitro protoplast transformation (as described, for example, in U.S. Pat. No. 4,684,611), plant RNA virus-mediated transformation (as described, for example, in European patent publication 0,067,553 and U.S. Pat. No. 4,407,956) and liposome-mediated transformation (as described, for example, in U.S. Pat. No. 4,536,475).

Preferably, a nuclear female-sterile male-fertile plant of this invention is provided by transforming a plant cell with a disarmed Ti-plasmid vector containing the foreign DNA sequence with a female-sterility DNA under the control of a first promoter and preferably a marker DNA under the control of a second promoter. The marker DNA can be upstream or downstream of the female-sterility DNA in the Ti-plasmid vector, but preferably, the two are adjacent to one another and are located between the border sequences or at least located to the left of the right border sequence of the Ti-plasmid vector, so that they are properly transferred together into the nuclear genome of the plant cell. However, if desired, the cell can initially be transformed with a foreign DNA sequence containing a female-sterility DNA and a first promoter and can subsequently be transformed with a marker DNA and a second promoter, inserted into or near the genetic locus of the female-sterility DNA in the cell's nuclear genome, or this transformation can be carried out vice versa. Suitable vectors for this purpose are the same as those discussed above for transforming cells with the foreign DMA sequence. The preferred vector is a disarmed Ti-plasmid vector.

The selection of the female-sterility DNA of this invention is not critical. A suitable female-sterility DNA can be selected and isolated in a well-known manner, so that it encodes the first RNA, protein or polypeptide which significantly disturbs adversely the proper metabolism and/or functioning and/or development of any cell of a flower and/or seed and/or embryo in which the female-sterility DNA is expressed, preferably leading thereby to the death of such cell. Preferred examples of female-sterility DNAs encode: RNases such as RNase T1 (which degrades RNA molecules by hydrolyzing the bond after any guanine residue) and Barnase; DNases such as an endonuclease (e.g., EcoRI); or proteases such as a papain (e.g., papain zymogen and papain active protein). Other preferred examples of female-sterility DNAs encode: ribonucleases such as $T_2$ (Kawata et al (1988) Eur. J. Biochem 176, 683–697) or Rh (Horiuchi et al (1988) J. Biochem 103, 408–418); or glycoproteins such as are encoded by the S1, S2, S3, S6 and S7 alleles, particularly of *Nicotiana alata* (McClure et al (1989) Nature 342, 955–957).

Other examples of female-sterility DNAs encode enzymes which catalyze the synthesis of phytohormones, such as: isopentenyl transferase which is an enzyme that catalyzes the first step in cytokinin biosynthesis and is encoded by gene 4 of Agrobacterium T-DNA; or one or both of the enzymes involved in the synthesis of auxin and encoded by gene 1 and gene 2 of Agrobacterium T-DNA. Yet other examples of female-sterility DNAs encode: glucanases; lipases such as phospholipase $A_2$ (Verheij et al (1981) Rev. Biochem. Pharmacol. 91, 92-203); lipid peroxidases; or plant cell wall inhibitors. Still other examples of female-sterility DNAs encode proteins toxic to plants cells, such as a bacterial toxin (e.g., the A-fragment of diphtheria toxin or botulin).

Still another example of a female-sterility DNA is an antisense DNA: i) which encodes a strand of DNA complementary to a strand of DNA that is endogenous to, and naturally transcribed in, the cells of the flower, seed or embryo if the plant of this invention and ii) which is under the control of an endogenous promoter as described, for example, in European patent publication 0,223,399. Such an antisense DNA can be transcribed into an RNA sequence capable of binding to the coding and/or non-coding portion of an RNA, naturally produced in the call of the flower, seed or embryo, so as to inhibit the translation of the naturally produced RNA. Examples of such an antisense DNA are the antisense DNAs of: the STMG-type genes, such as the STMG07 gene, the STMG08 gene, the STMG4B12 gene and the STMG3C9 gene of Example 2 herein; the KTI3 gene (Jofuku and Goldberg (1989) The Plant Cell 1, 1079–1093); a gene encoding a seed-specific storage protein, such as a 2S albumin (Krebbers et al (1988) Plant Physiol. 87, 859–866; Altenbach et al (1987) Plant Molecular Biol. 8, 239–250; (Scolfield and Crouch (1987) J. Biol. Chem. 262, 12202–12208); or a gene corresponding to cDNA clone pMON9608 (Gasser et al (1989) The Plant Cell 1, 15). Such antisense DNAs can be naturally expressed in flower, seed or embryo cells of the plant under the control of the endogenous promoter of the complementary endogenous DNA strand (or gene) of the plant, for example: in the style (with the antisense DNA of the STMGO7, STMGO8, STMG4B12 or STMG3C9 gene); in the embryo axis (with the antisense DNA of the KTI3 gene); in seeds (with the antisense DNA of a 2S albumin-encoding gene); and in ovule cells (with the antisense DNA of PMON9608).

A further example of a female-sterility DNA encodes a specific RNA enzyme (i.e., a so-called "ribozyme"), capable of highly specific cleavage against a given target sequence as described by Haseloff and Gerlach (1988) Nature 334, 585–591. Such a ribozyme is, for example, the ribozyme targeted against the RNA encoded by the STMG07 gene, the STMG08 gene, the STMG4B12 gene, the STMG3C9 gene, the KTI3 gene, a gene encoding a seed-specific storage protein such as a 2S albumin or the gene corresponding to cDNA clone pMON9608.

Still other examples of female-sterility DNAs encode products which can render the flowers, seeds and/or embryos susceptible to a specific disease, such as a fungus infection. Such a female-sterility DNA can be used in a plant, in which all other cells or tissues, in which the female-sterility DNA is not expressed, are resistant to the specific disease.

Yet another example of a female-sterility DNA comprises a combination of: 1) a first gene encoding a vital dependent RNA polymerase, such as TNV replicase (Meulewater et al (1990) Virology 177, 1–11), under the control of a first promoter of this invention; and 2) a negative strand (i.e., antisense DNA) of a second gene: i) which encodes a first protein or polypeptide of this invention that, when produced or overproduced in the plant cell of this invention, disturbs significantly cell metabolism, development and/or functioning, ii) which is fused at its 3' end to a viral RNA replication recognition sequence or so-called "vital subgenomic promoter", such as the TNV subgenomic promoter (Lexis et al (1990) J. of Virology 64 (4), 1726–1733); and iii) which is fused at its 5' end to, and under the control of, another suitable promoter, such as a first promoter of this invention, capable of directing expression of the negative strand in the plant cell of this invention. The viral subgenomic promoter sequence is specifically recognized by the viral dependent RNA polymerase encoded by the first gene. This recognition leads to the repeated replication of the negative strand of the second gene as a sense strand, which leads to the synthesis of the first protein or polypeptide. Both the first gene and the negative strand are provided in the nuclear genome of the plant cell of this invention. This can be achieved by one transformation event, by two consecutive transformation events, or by crossing a plant having the first gene inserted into its genome with a plant having the negative strand inserted into its genome.

By "foreign" with regard to the foreign DNA sequence of this invention is meant that the foreign DNA sequence contains a foreign female-sterility DNA and/or a foreign first promoter. By "foreign" with regard to a DNA, such as a female-sterility DNA and a first promoter, as well as a marker DNA, a second promoter and any other DNA in the foreign DNA sequence, is meant that such a DNA is not in the same genomic environment in a plant cell, transformed with such a DNA in accordance with this invention, as is such a DNA when it is naturally found in the cell of the plant, bacteria, animal, fungus, virus, or the like, from which such a DNA originates. This means, for example, that a foreign female-sterility DNA or marker DNA can be: 1) a nuclear DNA in a plant of origin; 2) endogenous to the transformed plant cell (i.e., from a plant of origin with the same genotype as the plant being transformed); and 3) within the same transcriptional unit as its own endogenous promoter and 3' end transcription regulation signals (from the plant of origin) in the foreign DNA sequence of this invention in the transformed plant cell; but 4) inserted in a different place in the nuclear genome of the transformed plant cell than it was in the plant of origin so that it is not surrounded in the transformed plant cell by the genes which surrounded it naturally in the plant of origin. A foreign female-sterility or marker DNA can also, for example, be: 1) a nuclear DNA in a plant of origin; and 2) endogenous to the transformed plant cell; but 3) in the same transcriptional unit as a different (i.e., not its own) endogenous promoter and/or 3' end transcription regulation signals in a foreign chimaeric DNA sequence of this invention in a transformed plant cell. A foreign female-sterility or marker DNA can also, for example, be: 1) a nuclear DNA in a plant of origin; and 2) endogenous to the transformed plant cell; but 3) in the same transcriptional unit as a heterologous promoter and/or 3' end transcription regulation signals in a foreign chimaeric DNA sequence of this invention in a transformed plant cell. A foreign female-sterility or marker DNA can also, for example, be heterologous to the transformed plant cell and in the same transcriptional unit as an endogenous promoter and/or 3' transcription regulation signals (e.g., from the nuclear genome of a plant with the same genotype as the plant being transformed) in a foreign chimaeric DNA sequence of this invention in a transformed plant cell. An example of a foreign female-sterility DNA could come from the nuclear genome of a plant with the same genotype as the plant being transformed and encode a catalytic enzyme, such as a protease or ribonuclease, that is endogenous to cells of the flowers, seeds and/or embryos of the plant being transformed, so that the enzyme is overproduced in transformed cells of the flowers, seeds and/or embryos in order to disturb significantly their metabolism, functioning and/or development. Preferably, the female-sterility DNA and the marker DNA are each heterologous to the plant cell being transformed.

By "heterologous" with regard to a DNA, such as a female-sterility DNA, a first promoter, a marker DNA, a second promoter and any other DNA in the foreign DNA sequence of this invention, is meant that such a DNA is not naturally found in the nuclear genome of cells of a plant with the same genotype as the plant being transformed. Examples of heterologous DNAs include chloroplast and mitochondrial DNAs obtained from a plant with the same genotype as the plant being transformed, but preferred examples are chloroplast; mitochondrial, and nuclear DNAs from plants having a different genotype than the plant being transformed, DNAs from animal and bacterial genomes, and chromosomal and plasmidial DNAs from fungal and viral genomes.

By "chimaeric" with regard to the foreign DNA sequence of this invention is meant that at least one of its female-sterility DNAs: 1) is not naturally found under the control of its first promoter for the one female-sterility DNA; and/or 2) is not naturally found in the same genetic locus as at least one of its marker DNAs. Examples of foreign chimaeric DNA sequences of this invention comprise: a female-sterility DNA of bacterial origin under the control of a first promoter of plant origin; and a female-sterility DNA of plant origin under the control of a first promoter of plant origin and in the same genetic locus as a marker DNA of bacterial origin.

By "flower" is meant to include the entire organ of a flower, as well as one or more of its individual parts such as its shoot axis, sepals, petals, male reproductive organs (or stamens) and female reproductive organs (or carpels), whose wholly or partly, retarded or arrested development in accordance with this invention prevents the development of viable seeds in the flower but not the development and propagation of its male gametes; by "female organ" is meant the entire organ of a flower that is involved in the production of female gametes and/or viable seeds and/or viable embryos, as well as one or more of its individual parts such as its ovule, ovary, style, stigma, corolla, disc, septum, calyx and placenta tissue. By "embryo" is meant to include the entire embryo of a plant, as well as one or more of its individual parts such as its embryo axis and embryo cotyledons.

So that the female-sterility DNA of this invention is expressed selectively in cells of the flowers, particularly one or more of their female organs, in cells of the seeds and/or in cells of the embryos of the plants of this invention, it is preferred that the first promoter, which controls the female-sterility DNA in the foreign DNA sequence, be a promoter capable of directing gene expression selectively in cells of the flowers, seeds and/or embryos of the plant. Such a flower-, seed- and/or embryo-specific promoter can be an endogenous promoter or an exogenous promoter and can be from the nuclear genome or from the mitochondrial or chloroplast genome of a plant cell. In any event, the first promoter is foreign to the nuclear genome of the plant cell, being transformed. Preferably, the first promoter causes the female-sterility DNA to be expressed only in cells of one or more specific tissues of the flowers, preferably one or more female organs thereof, or of the seeds or of the embryos, especially in style cells, ovary cells, septum cells, seedcoat cells, endosperm cells, embryo axis cells and/or embryo cotyledon cells.

The first promoter of this invention can be selected and isolated in a well known manner from a plant, to be rendered female-sterile, so that the first promoter directs expression of the female-sterility DNA selectively in cells of the flowers, seeds and/or embryos of the plant, so as to kill or disable the plant's flowers, seeds and/or embryos and render the plant incapable of producing fertile female gametes, viable seeds and/or viable embryos. The first promoter is preferably also selected and isolated so that it is effective to prevent expression of the female-sterility DNA in other parts of the plant that are not involved in the production of fertile female gametes, viable seeds and/or viable embryos, especially in male organs of the flowers, so that the plant remains male-fertile. For example, a suitable flower-specific (preferably female reproductive organ-specific), seed-specific or embryo-specific first promoter can be identified and isolated in a plant, to be made female-sterile, by:

1. searching for an mRNA which is only present in the plant during the development of its flowers, seeds or embryos, preferably its ovary, style, placenta, calyx, scutellum, septum, seedcoat, endosperm or embryo cotyledons;

2. isolating this flower-, seed- or embryo-specific mRNA;

3. preparing a cDNA from this specific mRNA;

4. using this cDNA as a probe to identify the regions in the plant genome which contain DNA coding for this specific mRNA; and then 5. identifying the portion of the plant genome that is upstream (i.e., 5') from the DNA coding for this specific mRNA and that contains the promoter of this DNA.

Examples of a first promoter of this invention are the *Nicotiana tabacum* promoters of the STMG-type genes, described in Example 2, which are style and/or stigma specific promoters. Other style-stigma specific first promoters from other plant species can be isolated from their genomes, using the STMG-type genes as a probe as in step 4, above. Under hybridizing conditions, such a probe will hybridize to DNA coding for a style-stigma specific mRNA in a mixture of DNA sequences from the genome of the other plant species (Maniatis et al (1982) Molecular Cloning. A Laboratory Manual. Ed. Cold Spring Harbor Laboratory). Thereafter, as in step 5 above, another style-stigma specific first promoter can be identified. Other style-specific promotors can be isolated from self-incompatibility genes, such as an S-gene, for example as isolated from *Nicotiana alata* (McClure et al (1989) Nature 342, 955–957). Other female organ-specific promoters can be identified using other female organ-specific cDNAs, such as cDNA clone pMON9608 (Gasser et al (1989) The Plant Cell 1, 15) that hybridizes exclusively with a gene expressed only in the ovules of tomato plants.

Other examples of such a first promoter are: the promoter of the KTI3 gene (Jofuku and Goldberg (1989) The Plant Cell 1, 1079–1093) which is an embryo axis-specific promoter; and the seed-specific promoters derived from genes encoding seed-specific storage proteins, such as the PAT2S promoters, for example PAT2S1, PAT2S2, PAT2S3 and PAT2S4 which are promoters of the four 2S albumin genes ("AT2S genes") of *Aribidopsis thaliana* (Krebbers et al (1988) Plant Physiol. 87, 859–866).

If more than one female-sterility DNA is present in the foreign DNA sequence of this invention, all the female-sterility DNAs can be under the control of a single first promoter, but preferably, each female-sterility DNA is under the control of its own separate first promoter. Where a plurality of female-sterility DNAs are present in the foreign DNA sequence, each female-sterility DNA can encode the same or different first RNA, polypeptide or protein. For example, when the female-sterility DNA encodes an RNase such as RNase T1, it is preferred that at least 3, particularly 4 to 6, copies of the female-sterility DNA and its first promoter be provided in the foreign DNA sequence. In such a case it is also preferred that all the female-sterility DNAs and their first promoters be adjacent to one another in the foreign DNA sequence and in any vector used to transform plant cells with the foreign DNA sequence. If the plurality of female-sterility DNAs encode different products, such as gene 1 and gene 2 or such as TNV replicase and a RNase, DNase or protease, it may be preferred that the female-sterility DNAs not be adjacent to one another and perhaps not even be present in the same vector used to transform plant cells with the foreign DNA sequence or even not present in the same parent plant of the female-sterile plant of this invention.

The selection of the marker DNA of this invention also is not critical. A suitable marker DNA can be selected and isolated in a well known manner, so that it encodes a second RNA, protein or polypeptide that allows plants or their tissue, seeds or even cells, expressing the marker DNA, to be easily distinguished and separated from plants or their tissue, seeds or even cells not expressing the second RNA, protein or polypeptide. Examples of marker DNAs encode proteins that can provide a distinguishable color to plant cells, such as the A1 gene encoding dihydroquercetin-4-reductase (Meyer et al (1987) Nature 330, 677–678) and the glucoronidase gene (Jefferson et al (1988) Proc. Natl. Aced. Sci. USA ("PNAS") 83, 8447), or that provide a specific morphological characteristic to the plant such as dwarf growth or a different shape of the leaves. Other examples of marker DNAs confer on plants: stress tolerance, such as is provided by the gene encoding superoxide dismutase as described in European patent application 88/402222.9; disease or pest resistance such as is provided by a gene encoding a *Bacillus thuringiensis,* endotoxin conferring insect resistance as described in European patent application 86/300291.1 or a gene encoding a bacterial peptide that confers a bacterial resistance as described in European patent application 88/401673.4.

Preferred marker DNAs encode second proteins or polypeptides inhibiting or neutralizing the action of herbicides such as: the sfr (SEQ. ID NO: 10, SEQ. ID NO: 11 ) gene and the sfrsv (SEQ ID No 12, SEQ ID No 13) gene encoding enzymes conferring resistance to glutamine synthetase inhibitors such as Biolaphos and phosphinotricine as described in European patent application 87/400,544.0; and genes encoding modified target enzymes for certain herbicides that have a lower affinity for the herbicides than naturally produced endogenous enzymes, such as a modified glutamine synthetase as a target for phosphinotricine as described in European patent publication 0,240,792 and a modified 5-enolpyruvylshikimate-3 phosphate synthase as a target for glyphosate as described in European patent publication 0,218,571. Other examples are: marker DNAs encoding proteins which neutralize the action of the herbicide bromoxynil (Stalker et al (1988) in: Genetic Improvements of Agriculturally Important Crops, Ed: R. T. Fraley, N. M. Frey and J. Schell, Cold Spring Harbor Laboratories); the herbicide sulfonylurea (Lee et al (1988) EMBO J. 7, 1241–1248); and the herbicide. 2,4 D (presented at the .2nd International Symposium of Plant Molecular Biology, Jerusalem, 13–18 Nov. 1988).

The second promoter of this invention, which controls the marker DNA, can also be selected and isolated in a well known manner so that the marker DNA is expressed either selectively in one or more specific tissues or specific cells or constitutively in the entire plant, as desired depending on the nature of the second RNA, protein or polypeptide encoded by the marker DNA, For example, if the marker DNA encodes an herbicide resistance, it may be useful to have the marker DNA expressed in all cells of the plant, using a strong constitutive second promoter such as a 35S promoter (Odell et al (1985) Nature 313, 810–812), a 35S'3 promoter (Hull and Howell (1987) Virology 86, 482–493), the promoter of the nopaline synthetase gene ("PNOS") of the Ti-plasmid (Herrera-Estrella (1983) Nature 303, 209–213) or the promoter of the octopine synthase gene ("POCS" [De Greve et al (1982) J. Mol. Appl. Genet. 1 (6), 499–511]). If the marker DNA encodes a protein conferring disease resistance, it may be useful to have the marker DNA selectively expressed in wound tissue by using, for example, a TR promoter such as the TR1' or TR2' promoter of the Ti-plasmid (Velten et al (1984) EMBO J. 3, 2723–2730). If the marker DNA encodes a herbicide resistance, it also may be useful to have the marker DNA selectively expressed in green tissue by using, for example, the promoter of the gone encoding the small subunit of Rubisco (European patent application 87/400,544.0). If the marker DNA encodes a pigment, it also may be useful to have the marker DNA expressed in specific cells such as petal cells, leaf cells or seed cells, preferably in the outside layer of the seed coat.

One can identify and isolate in a well known manner a tissue-specific second promoter for a plant to be rendered female-sterile and easily distinguishable from non-transformed plants by:

1. searching for an mRNA which is only present in the plant during the development of a certain tissue, such as its petals, leaves or seeds;

2. isolating this tissue-specific mRNA;

3. preparing a cDNA from this tissue-specific mRNA;

4. using this cDNA as a probe to identify the regions in the plant genome which contain DNA coding for the tissue-specific mRNA; and then 5. identifying the portion of the plant genome that is upstream from the DNA coding for the tissue-specific mRNA and that contains the promoter for said DNA.

If more than one marker DNA is present in the foreign DNA sequence of this invention, all the marker DNAs can be under the control of a single second promoter, but preferably, each marker DNA is under the control of its own separate second promoter. More preferably, each marker DNA is under the control of its own second promoter and encodes a different second RNA, protein or polypeptide, providing different distinguishable characteristics to a transformed plant. In some cases, it may be preferred that the marker DNA(s) and second promoter(s) are adjacent to each other and to the one or more female-sterility DNAs contained in the foreign DNA sequence of this invention and in any vector used to transform plant cells with the foreign DNA sequence. In other cases, it may be preferred that the marker DNAs are not adjacent to each ether and/or to the female-sterility DNAs.

It is generally preferred that the first RNA, protein or polypeptide, encoded by the female-sterility DNA, interfere significantly with the metabolism, functioning and/or development of the cells of the flowers and/or seeds and/or embryos by acting in the cytoplasm or the nucleus of these cells. However, when it is desired to have the first protein or polypeptide and/or the second protein or polypeptide transported from the cytoplasm into chloroplasts or mitochondria of the cells of transformed plants, the foreign DNA sequence can further include a first additional foreign DNA encoding a transit peptide. The first additional DNA is located between the female-sterility DNA and the first promoter if the first protein or polypeptide is to be so-transported and is between the marker DNA and the second promoter if the second protein or polypeptide is to be so-transported. By "transit peptide" is meant a polypeptide fragment which is normally associated with a chloroplast or mitochondrial protein or subunit of the protein that is produced in a cell as a precursor protein encoded by the nuclear DNA of the cell. The transit peptide is responsible for the translocation process of the nuclear-encoded chloroplast or mitochondrial protein or subunit into the chloroplast or the mitochondria, and during such a process, the transit peptide is separated or proteolytically removed from the chloroplast or mitochondrial protein or subunit. One or more of such first additional DNAs can be provided in the foreign DNA sequence of this invention for transporting one or more first or second proteins or polypeptides as generally described in European patent applications 85/402,596.2 and 88/402,222.9 and in: Van den Broeck et al (1985) Nature 313, 358–363; Schatz (1987) Eur. J. of Bioch. 165, 1–6; and Boutry et al (1987) Nature 328, 340–342. An example of a suitable transit peptide for transport into chloroplasts is the transit peptide of the small subunit of the enzyme RUBP carboxylase (European patent application 85/402,596.2), and an example of a transit peptide for transport into mitochondria is the transit peptide of the enzyme Mn-superoxide dismutase (see example 10 herein and European patent application 89/401, 194.9).

It is also generally preferred that the first RNA, protein or polypeptide, encoded by the female-sterility DNA, act intracellularly so as to interfere with cell metabolism, functioning and/or development in the plant. However when it is desired to have the first protein or polypeptide and/or the second protein or polypeptide secreted out of the intercellular areas of the plant cells, in which they are expressed, or out of the tissue, in which they are expressed, the foreign DNA sequence can further include a second additional foreign DNA encoding a secretory signal peptide. The second additional foreign DNA is located between the female-sterility DNA and the first promoter if the first protein or polypeptide is to be secreted and between the marker DNA and the second promoter if the second protein or polypeptide is to be secreted. By "secretory signal peptide" is meant a natural polypeptide fragment which is, particularly in eukaryotic cells, associated during translocation with proteins that are normally secreted from cells or an artificial polypeptide fragment which, when associated during translocation with a protein or polypeptide, provokes its secretion from cells. Examples of suitable secretory signal peptides are set forth in: Von Heijne (1986), NAR 14 (11), 4683–4690; Denecke et al (1990), The Plant Cell 2, 51–59; and Chrispeels and Taque (1990) International Review of Cytology, in press.

In the foreign DNA sequence of this invention, 3' transcription termination and polyadenylation signals can be selected in a conventional manner from among those which are capable of providing correct transcription termination and polyadenylation of mRNA in plant cells. The transcription termination and polyadenylation signals can be the natural ones of the gone to be transcribed but can also be foreign or heterologous. Examples of heterologous transcription termination and polyadenylation signals are those of the octopine synthase gene (Gielen et al (1984) EMBO J. 3, 835–845) and the T-DNA gene 7 (Velten and Schell (1985) Nucleic Acids Research ("NAR") 13, 6981–6998).

Also in accordance with this invention, plant cell cultures, containing the foreign DNA sequence of this invention, can be used to regenerate homozygous dominant female-sterile male-fertile plants by performing the necessary transformations on diploid (Chuong and Beversdorf (1985) Plant Sci. 39, 219–226) or on haploid cell cultures and then (for haploid cell cultures) doubling the number of chromosomes by well known techniques (e.g., with colchicine). See: Plant Tissue and Cell Culture, Plant Biology 3, A. R. Liss, Inc. N.Y. (1987). Thereby, the foreign DNA sequence will be in homozygous form in the nuclear genome of each of the so-transformed plant cells. This is preferred for plant cell cultures containing a female-sterility DNA under the control of a first promoter which directs gene expression at a given stage of development of the female gametes, such as ovules, especially after meiosis, or in cells derived from the female gametes, such as seed or embryo cells, so that the female-sterility DNA is present and can be expressed in all female gametes or plant cells derived therefrom.

Also in accordance with this invention, processes are provided for producing hybrid seeds which can be grown into hybrid plants. These processes involve crossing in an otherwise conventional manner: a) a nuclear female-sterile male-fertile plant of this invention, in which the first RNA, protein or polypeptide is expressed selectively in flowers, preferably in at least one female organ thereof, or in embryos; with b) a male-sterile female-fertile plant. Suitable male-sterile female-fertile plants are described in European Patent Application 89/401194.9 as having a nuclear genome, in which are stably integrated:

(a) a male-sterility DNA encoding a RNA, protein or polypeptide which, when produced or overproduced in a stamen cell of a plant, significantly disturbs adversely the metabolism, functioning and/or development of the stamen cell; and (b) a promoter capable of directing expression of the male-sterility DNA selectively in stamen cells of the plant, preferably in anther, pollen and/or filament cells, particularly in tapetum and/or anther epidermal cells; the male-sterility DNA being in the same transcriptional unit as, and under the control of, this promoter;

and which optionally has in the same genetic locus:

(c) another marker DNA encoding a RNA, protein or polypeptide which, when present at least in a specific tissue or in at least specific cells of the plant, renders the plant easily separable from other plants which do not contain this RNA, protein or polypeptide at least in the specific tissue or specific cells; and (d) another promoter capable of directing expression of the other marker DNA at least in the specific tissue or specific cells and being in the same transcriptional unit as, and controlling, the other marker DNA.

The female-sterile plants and male-sterile plants are planted at random, near to each other to increase the chances of cross-pollination, without the need for precise planting patterns. The harvested seed, which is capable of germinating, will be the result of the fertilization of the male-sterile plants by the female-sterile plants and will be 100% hybrid. When the foreign DNA sequences responsible for the female-sterility and male-sterility characteristics are present in heterozygous form in the nuclear genomes of the respective parent plants, plants groom from such hybrid seed will be: 25% fertile, 25% female-sterile, 25% male-sterile and 25% sterile. When the foreign DNA sequence-encoding female-sterility is present in the nuclear genome of the male-fertile parent plant in homozygous form—which is preferred when the first promoter is an ovule-, seed- or embryo-specific promoter—all the plants grown from such hybrid seed will be female-sterile.

Further in accordance with this invention, processes are provided for producing fruit without seeds by crossing in an otherwise conventional manner:

a) a nuclear female-sterile male-fertile plant of this invention, in which the first RNA, protein or polypeptide is expressed selectively in seeds and in which the foreign DNA sequence, encoding the first RNA, protein or polypeptide, is preferably in homozygous form in the nuclear genome of the plant; with b) a male-sterile female-fertile plant.

Plants, transformed with the female-sterility DNA and in some cases preferably also with the marker DNA encoding an herbicide resistance, stably integrated in the plants' nuclear genomes and transmissible throughout generations as dominant alleles in accordance with this invention, are alternatives to, and can provide advantages over, presently used cytoplasmic and nuclear male-sterility systems for breeding and producing hybrid crops. In this regard, female-sterile male-fertile plants can provide: 1) inhibited seed formation in crops, 2) hybrid seeds for crops which do not easily cross-pollinate, and 3) easier breeding of plant lines as discussed below.

1. Inhibition of Seed Formation

There exist a wide variety of crops cultivated by man in which the seed is an undesirable by-product.

a) When the economic product of a plant consists of its vegetative part. By inhibiting seed production, the plant's energy can be focused on vegetative biomass production. Examples are perennial plants (e.g. forage grasses, forage legumes and rubber trees), some annual plants (e.g., sugar cane and potato), and especially all crops that would normally flower and set seed before the economic product is harvested. Other examples are plants, obtainable through genetic engineering, which produce, within their vegetative tissues, proteins, polypeptides or other metabolites for pharmaceutical or industrial purposes.

b) When the economic product of a plant is its fruit and it is desirable that the fruit be seedless, either because of consumer preferences (e.g., in tomato, melon and citrus fruit) or because seed formation uses up biomass that could otherwise be stored in the fruit (e.g., for providing high solids in tomatoes to be processed). Since such crops require fruit formation, the seedless condition, which usually induces fruit abortion, has to be compensated for by the possibility of obtaining parthenocarpic fruit set. Natural parthenocarpic fruit inducing genes exist in some crops, such as tomato and melon.

c) When the plant is not grown for its seeds, but remaining propagules, after harvesting may give rise to seed formation. The regrowth from these seeds can cause a considerable weed problem in the next culture. This "weed" problem is particularly well known with sugar beet.

d) When the plant is grown for its flowers (e.g., cut flowers, pot plants or garden ornamentals). For these species, it is often desirable to avoid seed set. In the case of cut flowers or pot plants, fertilization of the flowers often induces an accelerated senescence of the petals. In case of garden ornamentals, the formation of fruits and seeds reduces the time span and the intensity of flowering.

2. Hybrid Seed Production

Engineered female-sterility is useful as a seed production tool in combination with natural cytoplasmic or nuclear male-sterility systems or engineered nuclear male-sterility systems for the production of commercial hybrid seeds in crops where the seed is not the economic harvest and which do not easily cross-pollinate (e.g., for forage grasses, forage legumes, sugar beet, and many vegetables). The breeding of nuclear female-sterile plants with male-sterile plants provides a better control of hybrid seed quality (e.g., no mistakenly harvested male rows) and a higher seed set by favoring cross-pollination through at random interplanting of male-sterile and female-sterile parent plants and does not need the use of a restorer of fertility. A strategy for such production of hybrid seeds (e.g., for sugar-beet) may include the following steps ("MS" stands for male-sterility, "FS" stands for female-sterility and "H" stands for herbicide resistance):

A. Development of the Female Parent line A

Aa) Transform line A with a foreign DNA including a male-sterility DNA under the control of a stamen specific promoter and adjacent thereto a marker DNA encoding herbicide resistance, according to European patent application 89/401,194.9, giving $A^{MSH/msh}$ Ab) Maintain line $A^{MSH/msh}$ through crossing with line $A^{msh/msh}$. This gives:

50% $A^{MSH/msh}$ (male-sterile, herbicide resistant) and

50% $A^{msh/msh}$ (fertile, herbicide sensitive).

B. Development of the Male Parent Line B

Ba) Transform line B with the chimaeric DNA sequence of this invention including a female-sterility DNA under the control of a first promoter which directs gene expression selectively in cells of a female organ of the plant and adjacent thereto a marker DNA encoding herbicide resistance, giving $B^{FSH/fsh}$.

Bb) Maintain line $B^{FSH/fsh}$ through crossing with $B^{fsh/fsh}$, yielding:

50% $B^{FSH/fsh}$ (female-sterile, herbicide resist.) and

50% $B^{fsh/fsh}$ (fertile, herbicide sensitive).

C. Producing the Hybrid Seed Crop

Ca) Planting seeds obtained in Ab) and Bb) at random.

Cb) Eliminating through spraying with the herbicide the undesirable genotype before cross- and self-pollination could occur.

Cc) Cross-pollination occurring:

$A^{MsH/msh} \times B^{FSH/fsh}$ giving 100% hybrid seeds with the following genotype:

25% $AB^{MSH/msh;\ FSH/fsh}$

25% $AB^{MSH/msh;\ fsh/fsh}$

25% $AB^{msh/msh;\ FSH/fsh}$

25% $AB^{msh/msh;\ fsh/fsh}$

This represents the commercially sold seed.

3. Easier Breeding a) without a marker DNA

The ability to obtain microspore-derived double haploids of most major crops allows the production of homozygous nuclear female-sterile lines in a more or less straightforward way (Chuong and Beversdorf (1985) Plant Sci. 39, 219–226). This makes it unnecessary in many cases to have a marker DNA within the same genetic locus of the nuclear genome of the cells of the plant as the female-sterility DNA. This is especially so if the homozygous female-sterile plant can be vegetatively multiplied (e.g., many vegetables).

b) with a marker DNA

In case the female-sterility DNA is in the same genetic locus of the nuclear genome of the transformed plant as a marker DNA (e.g., encoding herbicide resistance), homozygous female-sterile plants are technically superior to many other lines as tester parents in line evaluation programs. This is especially the case for crops where the seed is not the economic harvest and which can easily cross-pollinate. Indeed, these female-sterile plants allow the testing of many female- and male-fertile lines in close proximity to one another while making it easy to eliminate any self-pollinated seed from the different plant lines, being tested, from seeds resulting from crosses between the different lines.

The following Examples illustrate the invention. The figures referred to in the Examples are as follows:

FIG. 1A shows the cDNA sequence of the STMG07 gene of Example 1.

FIG. 1B shows the cDNA sequence of the STMG08 gene of Example 1.

FIG. 2A shows the cDNA sequence of the STMG4B12 gene of Example 1.

FIG. 2B shows the cDNA sequence of the STMG3C9 gene of Example 1.

FIG. 3 shows a map of the vector pMG100 of Example 4.

Figure 4:
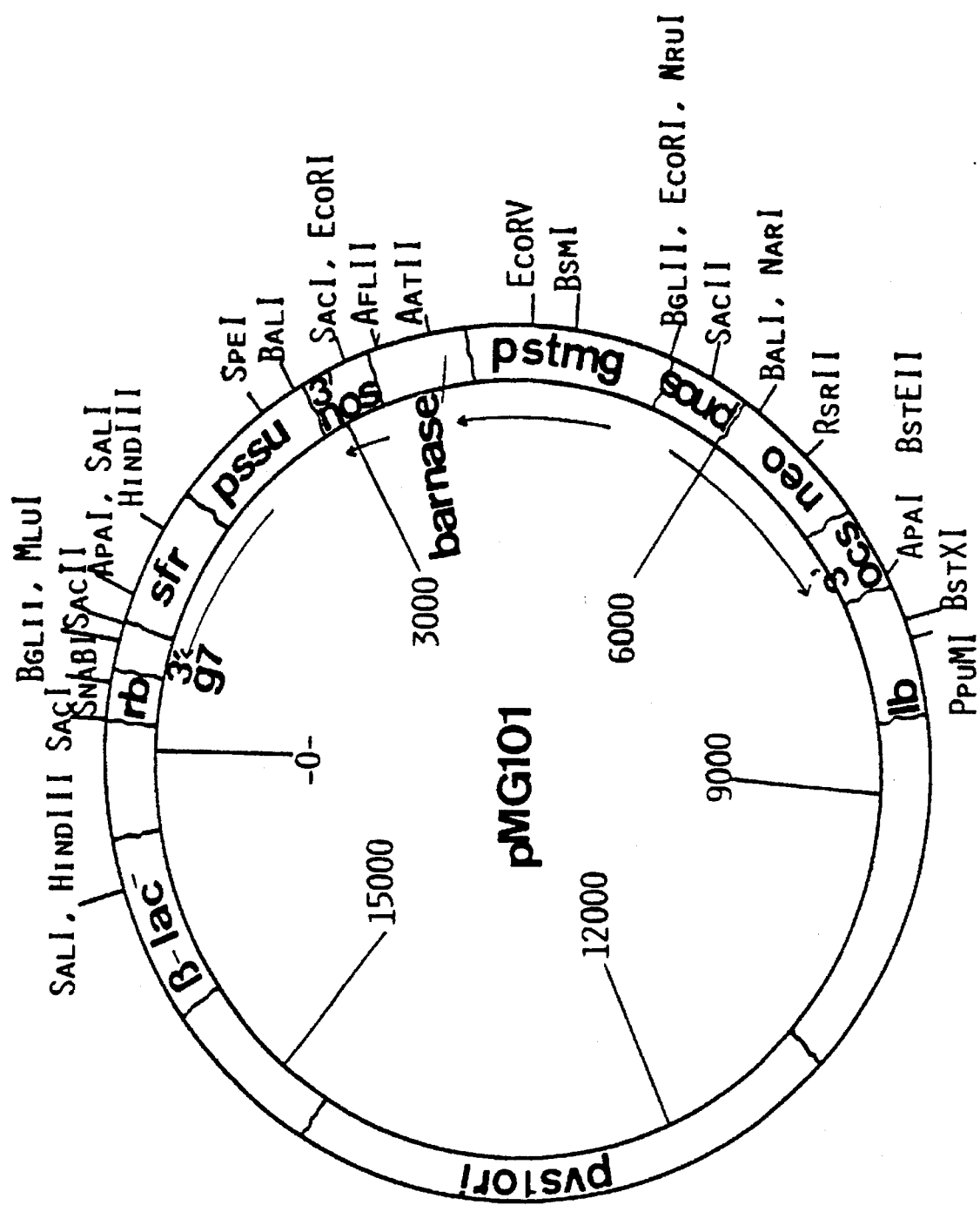
FIG. 4 shows a map of the vector pMG101 of Example 6.

FIG. 4 shows a map of the vector pMG101 of Example 6.

Figure 5:
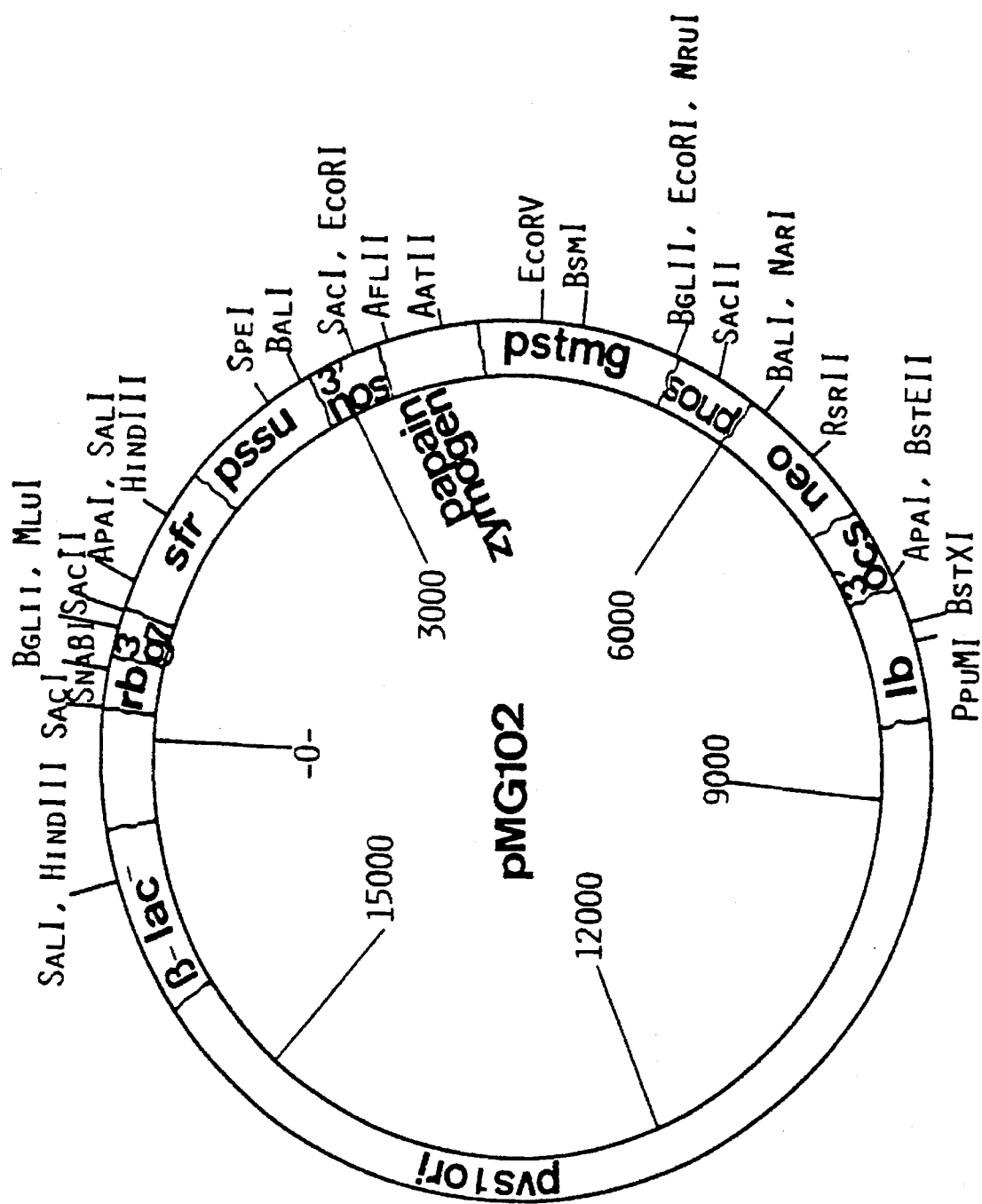
FIG. 5 shows a map of the vector pMG102 of Example 8.

FIG. 5 shows a map of the vector pMG102 of Example 8.

Figure 6:
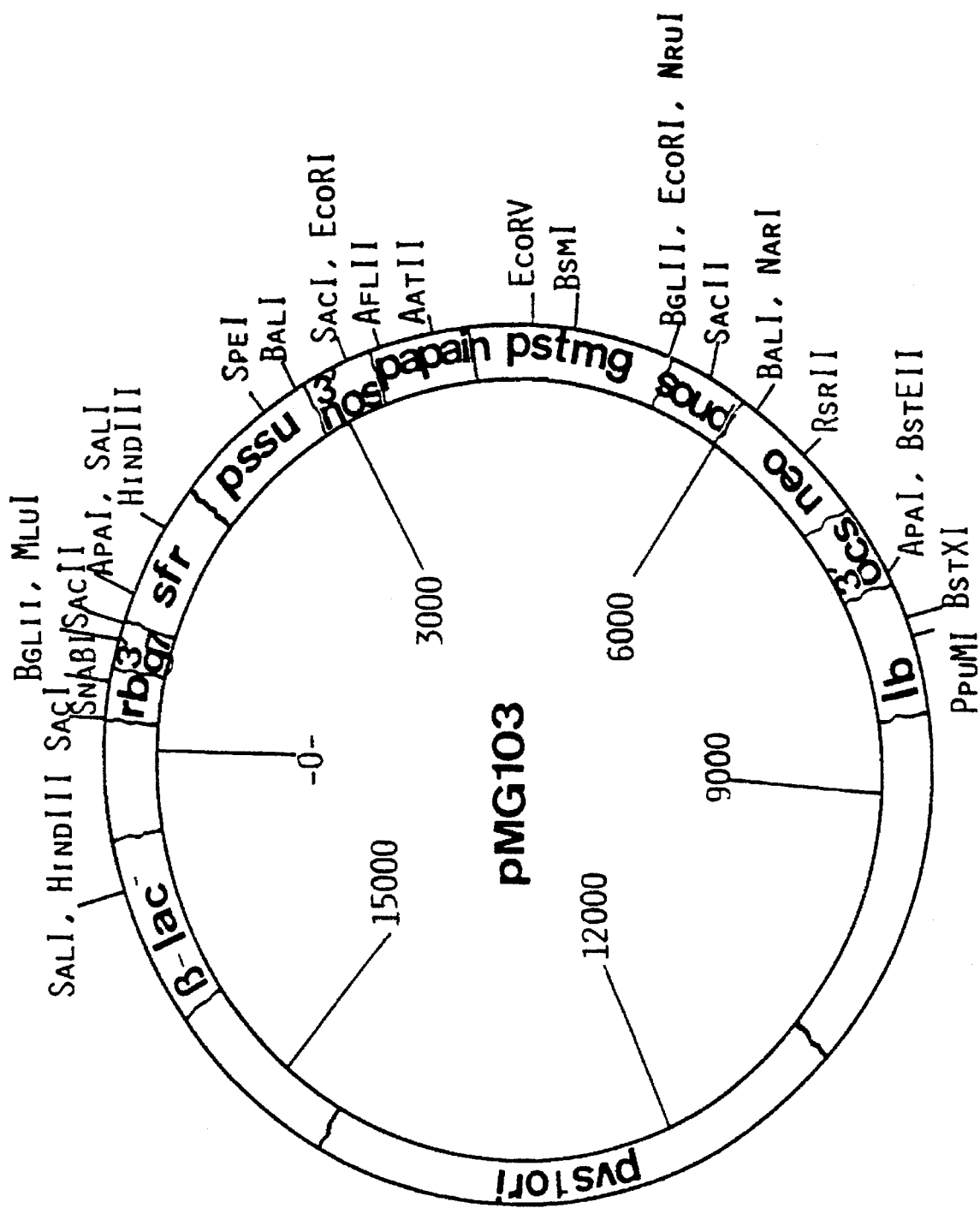
FIG. 6 shows a map of the vector pMG103 of Example 8.

FIG. 6 shows a map of the vector pMG103 of Example 8.

Figure 7:
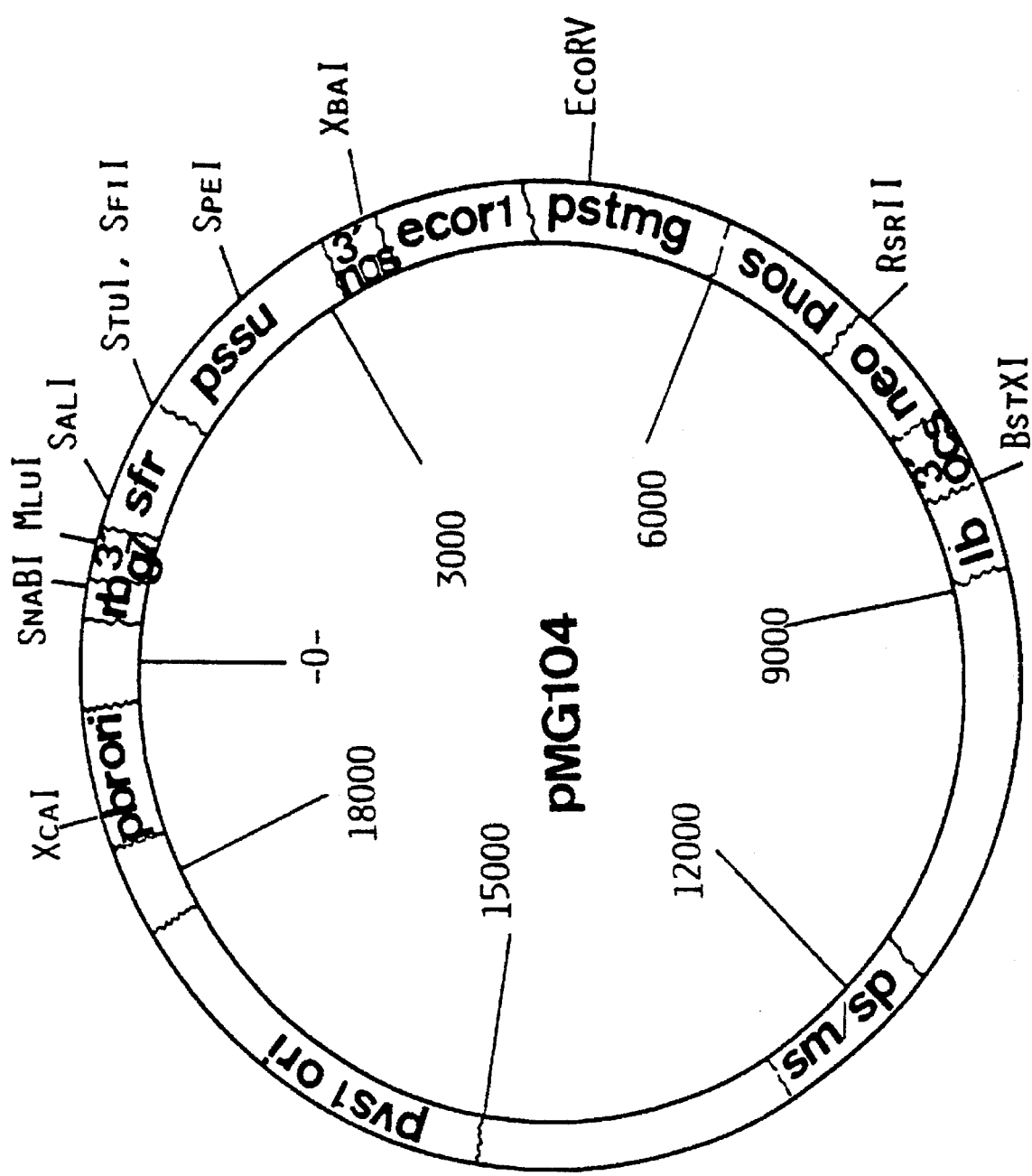
FIG. 7 shows a map of the vector pMG104 of Example 10.

FIG. 7 shows a map of the vector pMG104 of Example 10.

Figure 8:
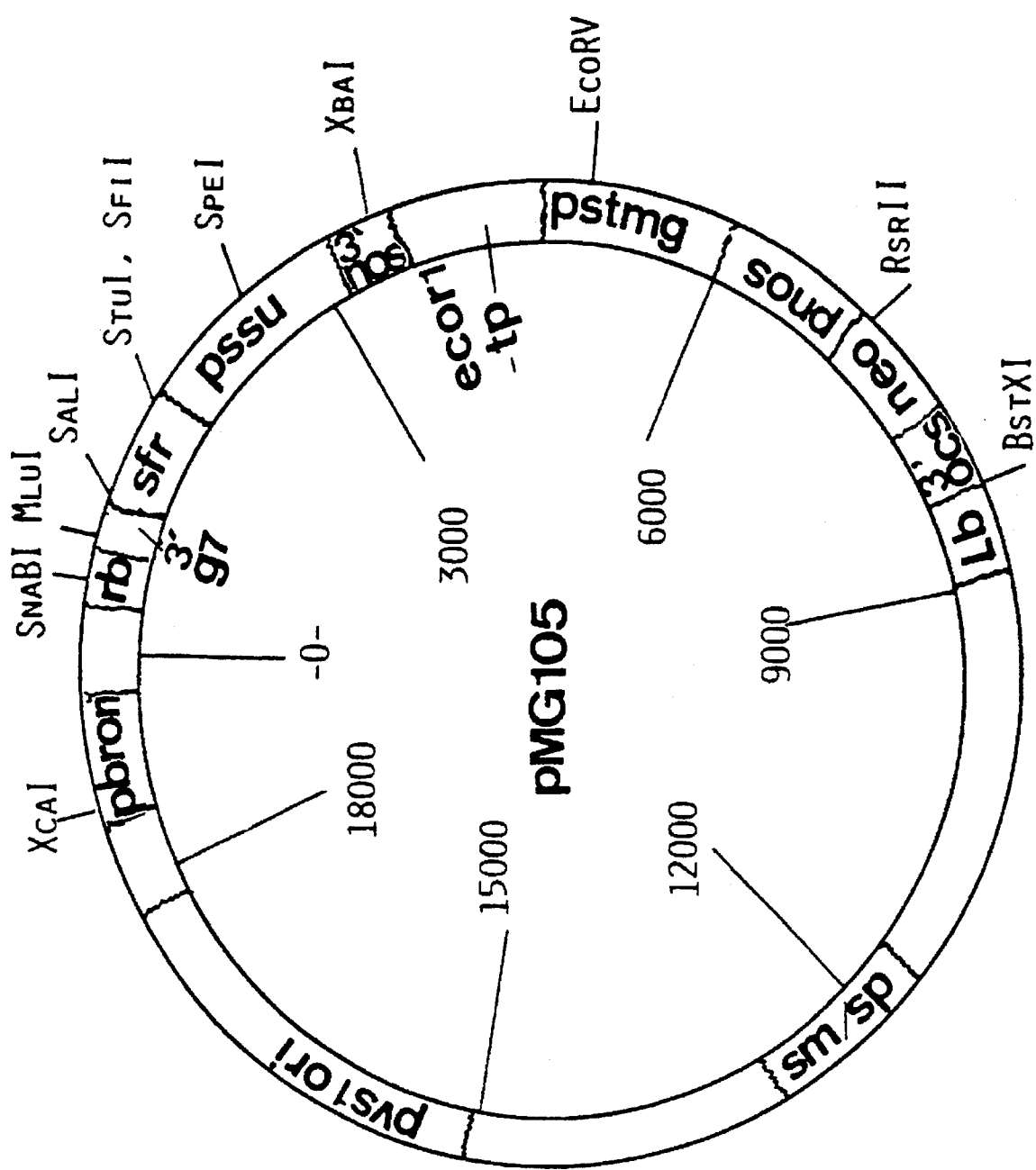
FIG. 8 shows a map of the vector pMG105 of Example 10.

FIG. 8 shows a map of the vector pMG105 of Example 10.

Unless otherwise stated in the Examples, all procedures for making and manipulating recombinant DNA were carried out by the standardized procedures described in Maniatis et al, *Molecular Cloning—A Laboratory Manual*, Cold

17

Spring Harbor Laboratory (1982). The following vector, used in the Examples, has been deposited in the Deutsche Sammlung Für Mikroorganismen und Zellculturen ("DSM"), Mascheroder Weg 1B, D-3300 Braunschweig, Federal Republic of Germany under the provisions of the Budapest Treaty:

| Vector | DSM Accession No. | Date |
| --- | --- | --- |
| pGSC1700 | 4469 | 21 Mar. 1988 |

EXAMPLE 1

Isolation of Style-stigma Specific cDNAs from *Nicotiana tabacum* "Petit Havana" SR1

Using well known procedures (Maniatis et al, 1982), total mRNA was isolated from the following different tobacco tissues: style-stigma tissues from flowers in stage 3 to 7 (according to Goldberg (1988) Science 240, 1460–1467); so-called "young stage" style-stigma tissues from a flower which did not develop pollen grains in stage 8 to 11 (according to Goldberg, 1988); so-called "old stage" ovary tissue from flowers in young stage; ovary tissue from flowers in old stage; and stem, root and leaf tissue from in vitro cultivated seedlings. cDNAs were synthesized from young and old style-stigma tissues using the Amersham (Amersham international PLC, Buckinghamshire, England) kit, cDNA Synthesis System Plus-RPN 1256 Y/Z, according to the directions set forth in the kit for its use. The cDNAs were cloned in Lambda gt 10 vector using the Amersham kit, cDNA Cloning System-lambda gt 10 - RPN 1257, according to the directions set forth in the kit. From the cDNA library thus obtained, differential screening was performed with a cDNA probe from seedlings on the one hand and a cDNA probe from style-stigma tissues on the other hand. The selected clones were subcloned in pGEM1 (Promega, Madison, Wis., USA). Probes of each of these subclones were prepared and first checked for their specificity in Northern blots with 10 ug of total mRNA from different tobacco tissues (roots, stems, leaves, sepals, petals, anthers, young stage style-stigma, old stage style-stigma, and old stage ovaries). The subclones, that specifically hybridized in these Northern blots with style-stigma mRNA, were again hybridized in Northern blots with 2 ug poly $A^+$ mRNA isolated from the above-mentioned tissues, including young ovaries, seeds and virus-infected leaves. The clones, called "pMG07" and "pMG08" and containing an insert of 0.963 kb and 0.472 kb, respectively, proved to be style-stigma specific cDNA sequences. These clones were sequenced, and their cDNA sequences are shown in FIG. 1A and FIG. 1B, respectively. The DNA sequence of pMG07 reveals the presence of one open reading frame ("ORF") over a sequence of 800 nucleotides. The sequence of pMG08 reveals an ORF over the total sequence.

From Prof. Goldberg of the University of California, Los Angeles (UCLA) were obtained: two *Nicotiana tabacum* style-stigma specific cDNAs (4B12 and 3C9) cloned as a PGtI - SmaI fragment in pGEM 3zf (−) (Promega, Madison, Wis., USA). These clones contained inserts of 0.748 kb and 1.046 kb, respectively. Probes of these two clones were hybridized in Northern blots with 10 ug of total mRNA from different tobacco tissues (roots, stems, leaves, sepals, petals, anthers, young stage style-stigma, old stage style-stigma, and old stage ovaries) in order to check their specificity.

18

These Northern blots confirmed the specificity of the clones and revealed that the transcript of 4B12 is 0.8 kb and that of 3C9 is 1.2 kb. The two clones were subcloned in pGEM1 (Promega), which subclones were called "pMG4B12" for the 4B12 clone and "pMG3C9" for the 3C9 clone. The subclones were again checked for their specificity in Northern blots with 2 ug poly $A^+$ mRNA isolated from the above-mentioned tissues, including young ovaries, seeds and virus-infected leaves. The clones pMG4B12 and pMG3C9, containing inserts of 0.748 kb and 1.046 kb, respectively, proved to be style-stigma specific sequences. These clones were sequenced and their cDNA sequences are shown in FIG. 2A and FIG. 2B, respectively.

EXAMPLE 2

Isolation of the Style-stigma Specific Genes ("STMG-type genes") Corresponding to the Style-stigma cDNA Clones Using known procedures (Maniatis et al, 1982), a probe from each of the cDNA clones of Example 1 of style-stigma specific sequences was used to isolate the corresponding genomic gene sequence which is specifically expressed in style-stigma tissues of the female organ of tobacco. According to protocols provided by Promega, tobacco genomic DNA was partially digested with Sau3A, and the restriction fragments were cloned into the lambda phage vector GEM.12 (Promega), digested with Xho I to produce genomic clones called "lambda STG07", "lambda STG08", "lambda STG4B12" and "lambda STG3C9". Subsequently, these genomic clones were subcloned in pGEM1 (Promega) according to the procedure of Promega. The subclones were again analyzed by Southern blot, using the respective cDNA clones as probes in order to identify the clones which contained the style-stigma specific DNA sequences. These subclones, called respectively "pSTG07", "pSTG08", "pSTG4B12" and "pSTG3C9" were sequenced (Maxam and Gilbert (1977) PNAS 74, 560). The orientation of these clones was determined by Northern blot analysis with riboprobes of both senses. Comparison of each cDNA sequence with its respective genomic clone sequence led to the identification of the region of homology. At the 5' end of each region, the ATG codon and the consensus sequence TATA were determined. That the "TATA" box is part of the promoter of the gene is confirmed by primer extention (Mcknight et al (1987) Cell 25, 385). The style-stigma specific genes, isolated using the style-stigma cDNA as probe, are called in general "STMG-type" genes. The style-stigma specific gene of pSTG07 is called "STMG07", that of pSTG08 is called "STMG08", that of pSTG4B12 is called "STMG4B12" and that of pSTG3C9 is called "STMG3C9".

EXAMPLE 3

Construction of Promoter Cassettes ("PSTMG") Derived From the Respective STMG-type Genes To construct chimaeric DNA sequences containing 5' regulator sequences, including the promoter of an STMG-type gene, in the same transcriptional unit as, and controlling, a first heterologous female-sterility DNA, cassettes are constructed by subcloning a DNA fragment including a promoter into the polylinker of pMAC 5–8 (European patent application 87/402348.4). This produces respective vectors which can be used to isolate single strand DNA for use in site directed mutagenesis.

Using site directed mutagenesis (European patent application 87/402348.4), the sequence surrounding the ATG initiation codon of each of the genes is modified in such a way that the mutation creates a given sequence which is a unique recognition site for a given restriction enzyme. The resulting plasmids each contain the newly created restriction site. The precise nucleotide sequence spanning the newly created restriction site is determined in order to confirm that it only differs from the 5' sequence of the corresponding STMG-type gene by the substitution, creating the new restriction site. The newly created promoter cassettes, each comprising a promoter, a 5' untranslated end of an STMG-type gene to its ATG initiation codon, and a new restriction site, are generally called "PSTMGs". The PSTMG containing the promoter and 5' end of STMG07 is called "PSTMG07", that of STMG08. is called "PSTMG08", that of STMG4B12 is called "PSTMG4B12" and that of STMG3C9 is called "PSTMG3C9".

EXAMPLE 4

Construction of Chimaeric DNA Sequences of a PBTMG and a RNAse T1 Gene

Plasmids named "pMG100", shown in FIG. 3, are constructed, each by assembling the following well known DNA fragments with a different one of the PSTMGs of Example 3:

1. a vector fragment, including T-DNA border sequences, from pGSC1700 in which the β-lactamase gene encoding ampicillin has been inactivated by insertion into the SacI site; located between the border sequences are the following DNA fragments 2–4;

2. a chimaeric sequence containing an Arabidopsis Rubisco SSU promoter ("PSSU" or "PSSUARA"), a herbicide resistance gene sfr (European patent application 87/400,544.0) and the 3' end (i.e., transcription termination) signals of a T-DNA gene 7 (Velten and Schell (1985) NAR 13, 6981);

3. a chimaeric sequence containing the EcoRI/SacI fragment from pGSFR401 which contains a nopaline-synthase promoter ("PNOS"), a neo gene encoding kanamycin resistance and the 3' end signals of an octopine synthase ("OCS") gene (European patent application 87/400,544.0 wherein pGSFR401 is called "pGSR4"); and 4. a chimaeric sequence, containing one of the PSTMG promoter cassettes from Example.3, fused in frame with a synthetic gene encoding RNase T1 from A. orhyzae, (Quaas et al, "Biophosphates and their Analogues-Synthese, Structure, Metabolism and Activity" (1987) Elsevier Science Publisher B. V., Amsterdam; Quaas et al (1988) Eur. J. Biochem. 173, 617–622) and the 3' end signals of a nopaline synthase ("NOS") gene (An et al (1985) EMBO J. 4 (2), 277).

Each pMG100 is a binary type T-DNA vector containing, within the T-DNA border sequences, three chimaeric sequences: PSSU-sfr and PNOS-neo which are marker DNAs with respectively PSSU and PNOS as second promoters; and PSTMG-RNase T1 gene which is a female-sterility DNA under the Control of a PSTMG as a first promoter. Expression of the female-sterility DNA under the control of the PSTMG promoter will produce RNase T1 selectively in style and/or stigma cells. This will be lethal for the style and/or stigma cells since the RNase T1 will degrade the RNA molecules which are indispensable for these cells metabolism.

EXAMPLE 5

Introduction of Each Chimaeric DNA Sequence of Example 4 into Tobacco and Alfalfa A recombinant Agrobacterium strain is constructed by mobilization of each pMG100 (from Example 4) from E. coli into Agrobacterium tumefaciens C58Cl Rif$^k$ containing pMP90 (Koncz and Schell (1986) Mol. Gen. Genetics 204, 383–396).

The resulting Agrobacterium strain, harboring pMP90 and pMG100, is used for the transformation of tobacco leaf discs (N. tabacum Petite Havane SR1), using standard procedures as described, for example, in European patent application 87/400,544.0, and of alfalfa according to the procedure described in D'Halluin et al (1990) Crop Science 30, in press. Carbonicillin is used to kill the Agrobacterium strains after co-cultivation. Transformed calli are selected on a substrate containing 5 mg/l phosphinotricin and 100 ug/ml kanamycin, and resistant calli are regenerated into plants. After induction of shoots and roots, which proves normal growth of the plants despite the presence of the RNase T1 gene, the transformants are transferred to the greenhouse and are grown until they flower. The flowers are examined and show no normal style-stigma formation. After pollination, no viable seeds are formed. The transformed plants are female-sterile.

EXAMPLE 6

Construction of Chimaeric DFA Sequences of a PSTMG and a Barnase Gene

Plasmids named "pMG101" shown in FIG. 4, are constructed, each by assembling the following well known DNA fragments with a different one of the PSTMGs of Example 3:

1. a vector fragment, including T-DNA border sequences, derived from pGSC1700 as described in Example 4 and with the following DNA fragments 2–4 between its border sequences;

2. the chimaeric sequence (no. 2) of Example 4, containing the PSSU promoter, the herbicide-resistance gene sfr and the 3' end of T-DNA gene 7;

3. the chimaeric sequence (no. 3) of Example 4, containing the PNOS promoter, the neo gone encoding kanamycin resistance and the 3' end signals of the OCS gene; and 4. a chimaeric sequence, containing one of the PSTMGs from Example 3, fused in frame with the Barnase gone from Bacillus amiloliquefaciens (Hartley and Rogerson (1972) Preparative Biochemistry 2 (3), 243–250) and the 3' end of the NOS gene of Example 4.

Each pMG101 is a binary type T-DNA vector containing, within the T-DNA border sequences, three chimaeric sequences: PSSU-sfr and PNOS-neo which are markers DNAs with respectively PSSU and PNOS as second promoters; and PSTMG-Barnase gene which is a female-sterility DNA under the control of a PSTMG as a first promoter. Plasmid pMG101 of FIG. 4, in which the PSTMG promoter is the 4B12 promoter, has been deposited at the BCCM/LMBP and has received accession number LMBP 3426. Expression of the female-sterility DNA under the control of the PSTMG promoter will produce Barnase selectively in style and/or stigma cells. This will be lethal for the style and/or stigma cells since Barnase will degrade the RNA molecules and thereby interfere with the metabolism of these cells.

EXAMPLE 7

Introduction of Each Chimaeric DNA Sequence of Example 6 into Tobacco and Alfalfa As described in Example 5, a recombinant Agrobacterium strain is constructed by mobilizing each pMG101 (from Example 6) from *E. coli* into Agrobacterium C58C1 Rif$^R$ containing pMP90 (Koncz and Schell (1986) Mol. Gen. Genetics 204, 383–396). The resulting strain, harboring pMP90 and pMG101, is used for tobacco leaf disc transformation and for alfalfa transformation. Transformed calli and shoots are selected using 5 mg/l phosphinothricin and 100 ug/ml kanamycin. That the Barnase gene is not expressed in the transformed herbicide-resistant calli and shoots is shown by their growth.

The transformed shoots are rooted, transferred to soil in the greenhouse and grown until they flower. The flowers of both the tobacco and alfalfa are examined, and essentially the same phenotype is observed in the transformed plants as is observed in the transformed plants described in Example 5 (i.e., no normal style-stigma formation). The transformed plants are female-sterile.

EXAMPLE 8

Construction of Chimaeric DNA Sequences of a PSTMG and a Gene Encoding Papain Plasmids named "pMG102", shown in FIG. 5, are constructed, each by assembling the following well known DNA fragments with a different one of the PSTMGs of Example 3:

1. a vector fragment, including T-DNA border sequences, derived from pGSC1700 as described in Example 4 and with the following DNA fragments 2-4 between its border sequences;

2. the chimaeric sequence (no. 2) of Example 4, containing the PSSU promoter, the herbicide resistance gene sfr and the 3' end of T-DNA gene 7.

3. the chimaeric sequence (no. 3) of Example 4, containing the PNOS promoter, the neo gene and the 3' end of the OCS gene; and 4. a chimaeric sequence, containing one of the PSTMGs from Example 3, fused in frame with:

a) a papain gene from *Carica papaya* fruit, encoding the papain zymogen which is a plant endopeptidase (Cohen et al (1986) Gene 48, 219–227) capable of attacking peptide, as well as ester, bonds; the following modifications are made in the DNA sequence of the papain gene according to Cohen et al (1986), using site directed mutagenesis as described in Example 3:

i. the nucleotide A, position-1 upstream of the first ATG codon, is mutated into nucleotide C in order to obtain a suitable NcoI cloning site; and ii. the GAA codons encoding glutamate at positions 47, 118 and 135 are mutated into CAA codons encoding glutamine; and b) the 3' end of the NOS gene of Example 4.

Each pMG102 is a binary type T-DNA vector containing, within the T-DNA border sequences, three chimaeric sequences: PSSU-sfr and PNOS-neo which are marker DNAs encoding dominant selectable markers for plant transformation under the control of respectively PSSU and PNOS as second promoters; and PSTMG-Papain zymogen gene which is a female-sterility DNA under the control of a PSTMG as a first promoter. Expression of the female-sterility DNA under the control of the PSTMG promoter will produce, selectively in style and/or stigma cells, an endopeptidase (the papain zymogen) that will cleave proteins in the style and/or stigma cells, thus leading to the death of these cells.

Plasmids named "pMG103", shown in FIG. 6, are also constructed, each by assembling the following well known DNA fragments with a different one of the PSTMGs of Example 3:

1. a vector fragment, including T-DNA border sequences, derived from pGSC1700 as described in Example 4 and with the following DNA fragments 2-4 between its border sequences;

2. the chimaeric sequence (no. 2) of Example 4, containing the PSSU promoter, the herbicide resistance gene sfr and the 3' end of -DNA gene 7;

3. the chimaeric sequence (no. 3) of Example 4, containing the PNOS promoter, the neo gene, and the 3' end of the OCS gene; and 4. a chimaeric sequence, containing one of the PSTMGs of Example 3, fused in frame with:

a) a papain gene from *Carica papaya* fruit, encoding the active protein of the papain zymogen; the following modifications are made in the DNA sequence of the papain gene according to Cohen et al (1986), using site directed mutagenesis as described in Example 3:

i. the AAT codon encoding Asn, upstream of the first Ile residue of the active protein, is mutated into a GAT codon, which provides a suitable EcoRV cloning site (GAT ATC). The EcoRV engineered site is fused directly to the PSTMG in order to obtain a direct in frame fusion of the promoter with the sequence encoding the active protein of the papain zymogen; and ii. the GAA codons encoding glutamate at positions 47, 118 and 135 are mutated into CAA codons encoding glutamine; and b) the 3' end of the NOS gene of Example 4.

Each pMG103, like each pMG102, is a binary type T-DNA vector containing, within the T-DNA border sequences, three chimaeric genes: PSSU-sfr and PNOS-neo encoding dominant selectable markers for plant transformation; and PSTMG-Papain active protein gene which is a female-sterility DNA that is under the control of a PSTMG as a first promoter and that encodes an endopeptidase that will cleave proteins in style and/or stigma cells, thus leading selectively to the death of these cells.

EXAMPLE 9

Introduction of Each Chimaeric DNA Sequence of Example 8 into Tobacco and Alfalfa As described in Example 5, each pMG102 and pMG103 (from Example 8) is mobilized from *E. coli* into separate Agrobacteria C58C1 Rif$^R$ carrying pMP90. The resulting strains, harboring pMP90 with pMG102 and pMP90 with pMG103, are used to transform tobacco and alfalfa following the procedures of Example 5. That the papain genes are not expressed in transformed herbicide- and kanamycin-resistant calli, shoots and roots is shown by their growth.

The transformed plants are transferred into the greenhouse and grown in soil until they flower. The flowers of both the tobacco and alfalfa are examined, and essentially the same phenotypes are observed in the transformed plants as are observed in the transformed plants described in Example 5 (i.e., no normal style-stigma formation). The transformed plants are female-sterile.

EXAMPLE 10

Construction of Chimaeric DNA Sequences of a PSTMG and a Gene Encoding EcoRI Plasmids named "pMG104", shown in FIG. 7, are constructed, each by assembling the following well known DNA fragments with a different one of the PSTMGs of Example 3:

1. a vector fragment, including T-DNA border sequences, derived from pGSC1701A2 (European patent application 87/115985.1); located between the border sequences are the following DNA fragments 2–5;
2. the chimaeric sequence (no. 2) of Example 4, containing the PSSU promoter, the herbicide-resistance gene sfr and the 3' end of T-DNA gene 7;
3. the chimaeric sequence (no. 3) of Example 4, containing the PNOS promoter, the neo gene and the 3' end of the OCS gene;
4. a chimaeric sequence, containing one of the PSTMGs of Example 3, fused in frame with:
   a) a gene encoding the EcoRI restriction endonuclease from an *E. coli* (Green et al (1981) J. Biol. Chem. 256, 2143–2153; Botterman and Zabeau (1985) Gene 37, 229–239) and capable of recognizing and cleaving the target sequence GAATTC on a double stranded DNA; the following modifications are made in the DNA sequence of the gene according to Green et al (1981) using site directed mutagenesis as described in Example 3:
      i. the nucleotides of the ATG initiation codon are replaced by ATGCA, creating a NsiI site at the initiation codon and yielding the following nucleotide sequences: ATGCA,TCT,AAT . . . (SEQ. ID NO: 5); and 1. a vector fragment, including T-DNA border sequences, derived from pGSC1701A2; located between the border sequences are the following DNA fragments 2–5;
2. the chimaeric sequence (no. 2) of Example 4, containing the PSSU promoter, the herbicide-resistance gone sfr and the 3' end of T-DNA gene 7;
3. the chimaeric sequence (no. 3) of Example 4, containing the PNOS promoter, the neo gene and the neo 3' end of the OCS gene;
4. a chimaeric sequence, containing one of the PSTMGs of Example 3, fused in frame with:
   a) a gene fragment encoding the transit peptide of the Mn-superoxide dismutase ("Mn-SOD") which is a NcoI-PstI fragment of a HpaI-HindIII fragment from pSOD1 (Bowler et al (1989) Embo J. 8, 31–38); the following modifications are made in the DNA sequence of the gene fragment according to Bowler et al (1989) using site directed mutagenesis as described in Example 3:
      i. the AA nucleotides located upstream at position -2 and -1 of the ATG initiation codon are changed to CC nucleotides creating a NcoI site at the initiation codon and yielding the following nucleotide sequences: —CCATGGCACTAC (SEQ. ID NO: 6) NcoI
      ii. the T,TCG,CTC nucleotides located immediately downstream of the processing site of the transit peptide are changed to C,TGC,AGC, creating a PstI site behind the processing site and yielding the following nucleotide sequences:

|                        |   | L   | Q   | T   | F   | S   | L   | (SEQ. ID NO:9) |
|------------------------|---|-----|-----|-----|-----|-----|-----|----------------|
| CTC, CGC, GGC,         |   | TTG, | CAG, | ACC, | TTT, | TCG, | CTC | (SEQ. ID NO:7) |
| CTC, CGC, GGC,         |   | TTG, | CAG, | ACC, | TTC, | TGC, | AGC | (SEQ. ID NO:8) |
|                        |   |     |     |     |     | PstI |     |                |

↓ ii. the HindII-HindIII fragment of the EcoRI gene cloned in pEcoR12 (Botterman and Zabeau, 1985) is cloned into the pMAC5-8 site directed mutagenesis vector; and b) the 3' end of the NOS gene of Example 4; and 5. a gene encoding an EcoRI methylase, under the control of its natural promoter (Botterman and Zabeau, 1985), which is capable of inhibiting the activity of EcoRI in *E. coli* or Agrobacterium, in order to overcome potential leaky expression of the EcoRI gene in microorganisms.

Each pMG104 is a binary type T-DNA vector containing, within the T-DNA border sequences, three chimaeric sequences: PSSU-sfr and PNOS-neo which are marker DNAs under the control of respectively PSSU and PNOS as second promoters; and PSTMG-EcoRI endonuclease gene which is a female-sterility DNA under the control of a PSTMG as a first promoter. Expression of the female-sterility DNA under the control of the PSTMG promoter selectively in style and/or stigma cells will produce the EcoRI restriction endonuclease which will cleave double stranded DNA at GAATTC sites (see for review of type II restriction modification systems: Wilson (1988) TIG 4 (11), 314–318) in the style and/or stigma cells, thus leading to the death of these cells.

Plasmids named "pMG105" are also constructed, each by assembling the following well known DNA fragments with a different one of the PSTMGs of Example 3:

in which the arrow indicates the processing site of the transit peptide sequence and the upper line the aminoacid sequence corresponding with the Mn-SOD coding sequence; the NcoI-PstI fragment is also fused in frame with a gene encoding the EcoRI restriction endonuclease from *E. coli* (Greene et al (1981) J. Biol. Chem. 256, 2143–2153; Botterman and Zabeau (1985) Gene 37, 229–239) and capable of recognition and cleavage of the target sequence GAATTC on a double stranded DNA, as found in pMG104; and b) the 3' end of the NOS gene of Example 4; and 5. a gene encoding the EcoRI methylase under the control of its natural promoter (Botterman and Zabeau, 1985), which is capable of inhibiting the activity of EcoRI in *E. coli* or Agrobacterium, in order to overcome potential leaky expression of the EcoRI gene in microorganisms, this gene being inserted into the vector fragment outside the border sequences.

Each pMG105 is a binary type T-DNA vector containing, within the border sequences, three chimeric sequences: PSSU-sfr and PNOS-NPIII which are marker DNAs under the control of respectively PSSU and PNOS as second promoters; and PSTMG-transit peptide-EcoRI endonuclease gene which is a female-sterility DNA having the PSTMG as a first promoter and a transit peptide-encoding sequence between them. Expression of the female-sterility DNA under the control of the PSTMG promoter selectively in style and/or stigma cells will produce a restriction endonuclease which will be targeted into the mitochondria of the style and/or stigma cells and cleave the double stranded DNA at the GAATTC sites in such cells. This will lead to the death of these cells.

EXAMPLE 11

Introduction of Each Chimaeric DNA Sequence of Example 10 into Tobacco and Alfalfa As described in Example 5, each pMG104 and pMG105 (from Example 10) is mobilized from *E. coli* into separate Agrobacteria C58C1 Rif$^R$ carrying pMP90. The resulting strains, harboring pMG104 with pMP90 and pMG105 with pMP90, are used to transform tobacco and alfalfa following the procedures described in Examples 5. That the EcoRI endonuclease genes are not expressed in transformed herbicide- and kanamycin-resistant calli, shoots and roots is shown by their growth.

The transformed plants are transferred into the greenhouse and grown in soil until they flower. The flowers of both the tobacco and alfalfa are examined, and essentially the same phenotypes are observed for the transformed plants as are observed in the transformed plants described in Example 5 (i.e., no normal style-stigma formation). The transformed plants are female-sterile.

Needless to say, this invention is not limited to the transformation of any specific plant(s). The invention relates to any plant, the nuclear genome of which can be transformed with a female-sterility DNA under the control of a first promoter that can direct expression of the female-sterility DNA selectively in cells of the flowers, particularly a female organ thereof, or the seeds or the embryos of the plant, whereby the plant can be both self-pollinated and cross-pollinated.

Also, this invention is not limited to the specific plasmids and vectors described in the foregoing Examples, but rather encompasses any plasmids and vectors containing the female-sterility DNA under the control of the first promoter.

Furthermore, this invention is not limited to the specific PSTMG promoters, described in the foregoing Examples, but rather encompasses any DNA sequence encoding a promoter capable of directing expression of the female-sterility DNA selectively in cells of flowers, particularly one or more female organs thereof, and/or seeds and/or embryos of the plant.

In addition, this invention is not limited to the specific female-sterility DNAs described in the foregoing Examples but rather encompasses any DNA sequence encoding a first RNA, protein or polypeptide which significantly disturbs adversely the metabolism, functioning and/or development of a cell of a flower, seed or embryo of a plant in which it is produced, under the control of the first promoter.

Also, this invention is not limited to the specific marker DNAs described in the foregoing Examples but rather encompasses any DNA sequence encoding a second RNA, protein or polypeptide which confers on at least a specific plant tissue or specific plant cells, in which such DNA sequence is expressed, a distinctive trait compared to such a specific plant tissue or specific plant cells in which such DNA sequence is not expressed.

We claim:

1. A female-sterile plant comprising a foreign DNA incorporated in the nuclear genome of its cells, wherein said foreign DNA comprises:
    (a) a female sterility DNA encoding a first protein or polypeptide which, when produced in cells of said plant, kills or significantly disturbs the metabolism, functioning or development of said cells; and
    (b) a first promoter which directs expression of said female-sterility DNA selectively in style cells, stigma cells or style and stigma cells of female reproductive organs of said plant, and which does not direct detectable expression of said female sterility DNA in the ovule or in other parts of said plant so that said plant remains male-fertile, said female sterility DNA being in the same transcriptional unit as, and under the control of said first promoter.

2. The plant of claim 1, wherein said foreign DNA further comprises:
    (c) a marker DNA encoding a marker RNA, or a marker protein or polypeptide which, when present at least in a specific tissue or in at least specific cells of said plant, renders said plant easily separable from other plants which do not contain said marker RNA, or said marker protein or polypeptide in said specific tissue or specific cells; and
    (d) a second promoter which directs expression of said marker DNA at least in said specific tissue or specific cells; said marker DNA being in the same transcriptional unit as, and under the control of, said second promoter.

3. The plant of claim 1, wherein said foreign DNA further comprises a DNA encoding a transit peptide which transports said first protein or polypeptide into a chloroplast or mitochondrion of said style cells, stigma cells or style/and stigma cells; said DNA being in the same transcriptional unit as said female-sterility DNA and said first promoter and between said female-sterility DNA and said first promoter.

4. The plant of claim 2, wherein said foreign DNA further comprises a DNA encoding a transit peptide which transports said marker protein or polypeptide into a chloroplast or mitochondrion of at least said specific tissue or specific cells; said DNA being in the same transcriptional unit as said marker DNA and said second promoter and between said marker DNA and said second promoter.

5. The plant of claim 1, wherein said female-sterility DNA encodes RNAse T1, barnase, papain active protein, or the A-fragment of diphtheria toxin.

6. The plant of claim 2, wherein said marker DNA is an herbicide resistance gene, a gene encoding a modified target enzyme for an herbicide having lower affinity for the herbicide, a gene encoding a protein or a polypeptide conferring a color to at least said specific tissue or specific cells, or a gene encoding a protein or a polypeptide conferring a disease or pest resistance.

7. The plant of claim 6, wherein said marker DNA is a sfr gene, a sfrsv gene, a GUS gene, or a gene encoding a *Bacillus thuringiensis* endotoxin.

8. The plant of claim 1, wherein said first promoter is PSTMG4B12 which normally directs transcription of an mRNA from which the CDNA having the nucleotide sequence of SEQ ID No. 3 can be prepared.

9. The plant of claim 2, wherein said second promoter is a constitutive promoter, a wound-inducible promoter, a promoter which directs gene expression selectively in plant tissue having photosynthetic activity, or a promoter which directs gene expression selectively in leaf cells, petal cells or seed cells.

10. The plant of claim 2, wherein said second promoter is a 35S promoter, a nos promoter, an ocs promoter, a TR1' promoter, a TR2' promoter, or a SSU promoter.

11. The plant of claim 1, wherein said foreign DNA is the T-DNA of the vector pMG101 of FIG. 4 in which the PSTMG promoter is the PSTMG 4B12 promoter, said vector being deposited at the BCCM/LMBP under accession number LMBP 3426.

12. The plant of claim 1, which is corn, potato, tomato, oilseed rape or other Brassica species, alfalfa, sunflower, cotton, celery, soybean, tobacco, or sugarbeet.

13. The plant of claim 1, wherein said female-sterility DNA encodes a ribonuclease.

14. The plant of claim 13, wherein said first promoter is PSTMG4B12 which normally directs transcription of an mRNA from which the cDNA having the nucleotide sequence of SEQ ID No. 3 can be prepared.

15. The plant of claim 13, wherein said foreign DNA further comprises:
    (c) a marker DNA which is a sfr or sfrsv gene; and,
    (d) a second promoter, which is a constitutive promoter or a promoter which directs expression selectively in plant tissue having photosynthetic activity; said marker DNA being in the same transcriptional unit as, and under the control of, said second promoter.

16. A female-sterile plant comprising a foreign DNA incorporated in the nuclear genome of its cells, wherein said foreign DNA comprises:
    (a) a female-sterility DNA encoding barnase; and,
    (b) a first promoter which directs expression of said female-sterility DNA selectively in style cells, stigma cells or style and stigma cells of the female reproductive organs of said plant, and which does not direct detectable expression of said female sterility DNA in the ovule or in other parts of said plant so that said plant remains male-fertile, said female sterility DNA being in the same transcriptional unit as, and under the control of, said first promoter.

17. The plant of claim 16, wherein said first promoter is PSTMG4B12 which normally directs transcription of an mRNA from which the cDNA having the nucleotide sequence of SEQ ID No. 3 can be prepared.

18. The plant of claim 2, wherein said female-sterility DNA encodes a RNAse, a DNAse, a bacterial toxin, a protease, or a glucanase.

19. A seedless fruit of a plant of claim 1, wherein said fruit comprises said foreign DNA.

20. A plant cell of the plant of claim 1, wherein said plant cell comprises said foreign DNA.

21. A recombinant DNA which comprises a first chimeric DNA which comprises:
    (a) a female sterility DNA encoding a first protein or polypeptide which, when produced in cells of a plant, kills or significantly disturbs the metabolism, functioning or development of said cells; and
    (b) a first promoter which directs expression of said female-sterility DNA selectively in style cells, stigma cells or style and stigma cells of the female reproductive organs of a plant and which does not direct detectable expression of said female sterility DNA in the ovule or in other parts of said plant, said female sterility DNA being in the same transcriptional unit as, and under the control of said first promoter.

22. The recombinant DNA of claim 21, which further comprises a second chimeric DNA, said second chimeric DNA comprising:

(c) a marker DNA encoding a marker RNA, or a marker protein or polypeptide which, when present at least in a specific tissue or in at least specific cells of said plant, renders said plant easily separable from other plants which do not include said marker RNA, or said marker protein or polypeptide in said specific tissue or specific cells; and (d) a second promoter which directs expression of said marker DNA at least in said specific tissue or specific cells; said marker DNA being in the same transcriptional unit as, and under the control of, said second promoter.

23. The recombinant DNA of claim 21, wherein said first chimeric DNA further comprises a DNA encoding a transit peptide which transports said first protein or polypeptide into a chloroplast or mitochondrion of said style cells, stigma cells or style and stigma cells; said DNA being in the same transcriptional unit as said female-sterility DNA and said first promoter and between said female-sterility DNA and said first promoter.

24. The recombinant DNA of claim 22, wherein said second chimeric DNA further comprises a DNA encoding a transit peptide which transports said marker protein or polypeptide into a chloroplast or mitochondrion of at least said specific tissue or specific cells; said second DNA being in the same transcriptional unit as said marker DNA and said second promoter and between said marker DNA and said second promoter.

25. The recombinant DNA of claim 21, wherein said female-sterility DNA encodes RNAse T1, barnase, papain active protein, or the A-fragment of diphtheria toxin.

26. The recombinant DNA of claim 21, wherein said female-sterility DNA encodes barnase.

27. The recombinant DNA of claim 22, wherein said marker DNA is a herbicide resistance gene.

28. The recombinant DNA of claim 22, wherein said marker DNA is an sfr or sfrsv gene.

29. A vector suitable for the transformation of plant cells which comprises the recombinant DNA of claim 21.

30. A vector suitable for transforming a cell of a plant capable of being infected with Agrobacterium, wherein said vector is pMG101 of FIG. 4, in which the PSTMG promoter is the PSTMG 4B12 promoter and is deposited at the BCCM/LMBP under accession number LMBP 3426.

31. A process for producing a female-sterile plant which comprises the steps of:
    a) introducing the recombinant DNA of claim 21, into a nuclear genome of a plant cell to obtain a transformed plant cell; and
    b) regenerating said female-sterile plant from said transformed plant cell.

32. A process for producing a seed comprising the steps of:
    a) pollinating a female-fertile plant with pollen from the female-sterile plant of claim 1; and
    b) recovering the seed from said female-fertile plant.

33. A process for producing a seed which comprises the steps of:
    (a) pollinating a female-fertile plant with pollen from the female-sterile plant of claim 2, wherein said female-fertile plant does not contain said marker DNA; and
    (b) recovering the seed from said female-fertile plant.

34. A process for producing a seed which comprises the steps of:
    a) pollinating a female-fertile plant with pollen from the female-sterile plant of claim 2, in which said marker DNA is a herbicide resistance gene or a gene encoding a modified target enzyme for said herbicide, wherein said female-fertile plant does not contain said marker DNA; and
    b) recovering the seed from said female-fertile plant.

35. A process according to claim 34, in which said marker DNA is a gene capable of conferring resistance to a glutamine synthetase inhibitor.

36. The process according to claim 35, wherein said marker DNA is a sfr gene.

37. The process according to claim 35, wherein said marker DNA is a sfrsv gene.

38. The process of claim 34, wherein said foreign DNA in said female-sterile plant comprises in addition to said marker DNA at least one other marker DNA and said female-fertile plant does not comprise said other marker DNA.

39. The process according to claim 32, in which the female-fertile plant is male-sterile.

40. The process according to claim 35, wherein said glutamine synthetase inhibitor is phosphinothricin.

41. The recombinant DNA of claim 21 wherein said first promoter is PSTMG4B12 which normally directs transcription of an mRNA from which the cDNA having the nucleotide sequence of SEQ ID No 3 can be prepared.

42. The recombinant DNA of claim 26 wherein said first promoter is PSTMG4B12 which normally directs transcription of an mRNA from which the cDNA having the nucleotide sequence of SEQ ID No 3 can be prepared.

43. A hybrid seed comprising the recombinant DNA of claim 21.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 963 base pairs
( B ) TYPE: nucleic acid
( C ) STRANDEDNESS: double
( D ) TOPOLOGY: linear ( i i ) MOLECULE TYPE: cDNA to mRNA ( v i i ) IMMEDIATE SOURCE:
( B ) CLONE: pmg07

( x i ) SEQUENCE DESCRIPTION: SEQ ID NO:1:

```
GAATTCCCAT  TGCCTTTCGA  ATTGCCACCA  GCGGAGATCC  CATTGCCGGA  GATCCCATTG       60
CCTTTCGATG  GGCCTACATT  CGTGCTACCG  CCACCATCAC  CACCACCACC  TCCATCGTCA      120
CCATCTCCAT  CTCCAGCAAA  GCAATCACCA  CCACCTCCTC  GGGCACCATC  ACCATCACCA      180
GCTACTCAGC  CACCTATAAA  GCAACCGCCA  CCACCAAGTG  CTAAGAAATC  TCCTCCGCCA      240
CCAGTTGCTT  ATCCACCAGT  TATGGCACCA  TCTCCATCAC  CGGCTGCTGA  GCCACCTATT      300
ATAGCACCAT  TTCCATCACC  AACAGCGAAT  CTACCCCTTA  TTCCCCGTCG  ACCAGCACCA      360
CCAGTAGTTA  AGCCGCTTCC  ACCTTTGGGG  AAGCCCCCTA  TCGTCAATGG  CCTTGTTTAT      420
TGTAAATCCT  GCAACAGCTA  TGGGTTCCCC  ACTCTGCTCA  ACACCTCCCT  ACTCCAGGA      480
GCTGTTGTGA  AACTAGTTTG  CTACAACGGA  AAGAAAACAA  TGGTTCAATC  GGCGACGACA      540
```

```
GACAACAAAG  GTGAGTTTCG  GATCATTCCC  AAATCATTAA  CCAGAGCAGA  TGTTGGCAAG      600

TGCAAGTTAT  ATTTAGTGAA  ATCACCAAAT  CCAAATTGCA  ATGTCCCAAC  AAATTTCAAT      660

GGTGGAAAAT  GTGGTGGTTT  ATTGAAGCCT  CTCCTACCAC  CTAAACAACC  GATTACCCCT      720

GCCGCTGTCC  CTCTATCTGA  TTTATATGGT  GTTGGACCTT  TTATATTTGA  AGCCTCCAGC      780

AAAATGCCAT  GCGATAAGAA  TTGAGCTCCT  CATTACTAGA  GCGATAATGT  ATAAGAGCAT      840

GAGTTTGTGA  CGGAAATTAT  TTTTTCTTT   TTGTTCTAT   AGTTATACA   AGGAGACAGA      900

AAACTTTGTA  TCACTATACA  GAAATCAAAT  GAGTCGCAAA  AGTCAAAATC  GAATTTATGA      960

AAA                                                                        963
```

( 2 ) INFORMATION FOR SEQ ID NO:2:

( i ) SEQUENCE CHARACTERISTICS:
        ( A ) LENGTH: 472 base pairs
        ( B ) TYPE: nucleic acid
        ( C ) STRANDEDNESS: double
        ( D ) TOPOLOGY: linear ( i i ) MOLECULE TYPE: cDNA to mRNA ( v i i ) IMMEDIATE SOURCE:
        ( B ) CLONE: pmg08

( x i ) SEQUENCE DESCRIPTION: SEQ ID NO:2:

```
GAATTCCGGC  TTTTACATCA  GTAAAGATCC  TAGTGCTCAT  ACAAGTTTCA  GTTTTAGCAC       60

TCAGCTCATT  CTCAGAGCTT  AGCTTTGGTA  AAGGAATTGA  AAGCTCGTCA  TTAGACAAAG      120

GACAACACCA  TCCAATCTTC  TCAACAGTTC  ACTTATTCTT  TGGAAAGTCT  CCCAAGAAAA      180

GCCCCTCTAG  CCCTACACCG  GTAAACAAGC  CATCACCATC  ACCACCACCA  CAGGTTAAGT      240

CATCCCTTCC  GCCGCCTGCT  AAGTCACCAC  CGCCGCCACC  AGCTAAGTCA  CCACCTCCTC      300

TGCTGCCTCC  ACCACCATCT  CAACCACCAA  ACAACCACC   TCCACCTCCG  CCGCCACCAG      360

CAAAGCAACC  ACCATCTGCT  AAGCCACCTA  TTAAACCTCC  ATCTCCGTCA  CCGGCTGCTC      420

AGCCACCAGC  AACGCAACGA  GCAACACCAC  CACCGGCAAT  GCAACGGGCA  CC               472
```

( 2 ) INFORMATION FOR SEQ ID NO:3:

( i ) SEQUENCE CHARACTERISTICS:
        ( A ) LENGTH: 748 base pairs
        ( B ) TYPE: nucleic acid
        ( C ) STRANDEDNESS: double
        ( D ) TOPOLOGY: linear ( i i ) MOLECULE TYPE: cDNA to mRNA ( v i i ) IMMEDIATE SOURCE:
        ( B ) CLONE: 4B12

( x i ) SEQUENCE DESCRIPTION: SEQ ID NO:3:

```
GCCCTGTAGC  GGCATTAAGC  GCGGCGGGTG  TGGTGGTTAC  GCGCAGTGAC  CGCTACACTT       60

GCCAGCGCCC  TAGCGCCCGC  TCCTTTCGCT  CTTCTCATTC  TCATCATCCT  CACTCTTTCT      120

AGCACACCAA  TTACCACAAT  GTCTATACCC  GAGACAAACC  GTAGAAATGC  AACTACAAAC      180

TCTTACACCG  ATGTTGCTCT  TTCTGCGCGA  AAAGGTGCAT  TCCTCCTCC   CAGAAAGCTA      240

GGAGAATACT  CGACAAATTC  TACCGACTAC  AACTTGATCT  GCAAACTTG   CAAGAGATTA      300

TCGGAACGCA  ATACATGTTG  TTTCAACTAC  AGTTGTGTTG  ATGTGTCCAC  CAACAGGTTC      360

AACTGTGGCT  CCTGTGGCCT  TGTCTGTAAC  CTTGGAACGA  GATGCTGTGG  TGGGATCTGT      420

GTGGACATCC  AGAAAGACAA  TGGCAATTGT  GGCAAGTGTT  CTAATGTTTG  CTCTCCTGGT      480
```

| | | | | | |
|---|---|---|---|---|---|
|CAGAAGTGTT|CATTTGGGTT|TTGTGACTAT|GCCTAAGTAT|ATTTTCCCTA|TGTCTAGTAA 540|
|TAACCAGAGT|CTGTGTAAGC|CTGTCAAATA|ACTAACTCCC|CTGTCCCTAG|GGTGAAATGT 600|
|TACTCTAATA|ACGTTGGAGA|TTTGCATTCT|GTGTTGTTTG|TAGTAAGTTA|TGGCTAGTAA 660|
|TCTATTTAAG|GTGACTTGGA|ATACATAAAA|AAAAAAAAA|AAAAAAAAA|AAAAAAAAA 720|
|AAAAAAAAA|AAAAAAAAA|AAAATGCA| | | 748|

( 2 ) INFORMATION FOR SEQ ID NO:4:

( i ) SEQUENCE CHARACTERISTICS:
    ( A ) LENGTH: 1046 base pairs
    ( B ) TYPE: nucleic acid
    ( C ) STRANDEDNESS: double
    ( D ) TOPOLOGY: linear ( i i ) MOLECULE TYPE: cDNA to mRNA ( v i i ) IMMEDIATE SOURCE:
    ( B ) CLONE: 3C9

( x i ) SEQUENCE DESCRIPTION: SEQ ID NO:4:

| | | | | | |
|---|---|---|---|---|---|
|CCCTTGTTCT|TTTTCAGCTT|TCAGTTTTAT|TACTTAGCTC|ATTCACAGTA|GTTCTTAGCC 60|
|AGGAGGAAGA|CATTGGGGGT|TGGTTTACCA|CCAAACATCA|TGACCACCTT|TCACCAGCTC 120|
|AAGCTCCTAA|GCCTCACAAA|GGCCACCACC|ACCCCAAACA|TTCCCCAGCC|CCTTCACCAA 180|
|CTAAGCCTCC|CACTTATAGC|CCATCGAAAC|CACCAGTTAA|ACCACCGGTT|AAACCACCAA 240|
|CTAAGGCTCC|CACTTATAGC|CCATCAAAAC|CACCAGCTAA|GCCACCAGTT|AAACCACCAA 300|
|CACCAACACC|ATCACCTTAT|CCTGCTCCTG|CTCCTATTAC|TAGGAAACCT|GTAGCAGTCC 360|
|GTGGCCTTGT|TTACTGCAAG|CCGTGCAAGT|TTAGAGGGGT|TAAAACTCTA|AACCAAGCTT 420|
|CCCCACTCCT|GGGTGCGGTA|GTGAAGCTAG|TATGCAACAA|CACAAAGAAG|ACATTAGTGG 480|
|AACAGGGCAA|GACAGACAAG|AATGGCTTCT|TCTGGATCAT|GCCCAAATTC|TTGTCCTCAG 540|
|CAGCTTACCA|CAAATGCAAG|GTGTTCTTGG|TCTCATCAAA|CAATACTTAC|TGTGATGTCC 600|
|CAACAGATTA|CAATGGTGGA|AAATCTGGTG|CTTTGTTGAA|ATACACCCCA|CTTCCTAAGC 660|
|CACCAGCAGC|TACTTCTCTC|CCTGTTAAAC|TCCCCACATT|TGATGTCTTC|ACTGTTGGAC 720|
|CTTTTGGTTT|CGAACCCTCA|AAGAAGGTGC|CATGCAAAAA|GTAACTTGCA|TGGGAATTA 780|
|GAAAGATAGG|AAGGAAAAAT|TAATTATGTG|TTGAAGAAAG|ACGATTATGT|ACCTGTTTCC 840|
|TGTGTTCTTG|TTATTATTTT|ATTAATAAAT|GAAGCAAAGA|GGAAAGAACG|TAGTTTTCTT 900|
|GTTTTCCTAT|TTTGTTTCTC|TCTATCAAAA|CCCAACAAGT|AAAATGGATT|TATAAGTTTT 960|
|TCTTCAAAAA|AAAAAAAAA|AAAAAAAAA|AAAAAAAAA|AAAAAAAAA|AAAAAAAAA 1020|
|AAAAAAAAA|AAAAAATGCA|GGTCGA| | | 1046|

( 2 ) INFORMATION FOR SEQ ID NO:5:

( i ) SEQUENCE CHARACTERISTICS:
    ( A ) LENGTH: 11 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc = "mutated & translation
      initiation region of EcoRI gene"

( x i ) SEQUENCE DESCRIPTION: SEQ ID NO:5:

ATGCATCTAA T                        11

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "region around translation
            initiation site of MnSOD gene"

( i x ) FEATURE:
        ( A ) NAME/KEY: -
        ( B ) LOCATION: 1..6
        ( D ) OTHER INFORMATION: /label=NcoI
            / note= "recognition sequence of NcoI"

( i x ) FEATURE:
        ( A ) NAME/KEY: -
        ( B ) LOCATION: 3..5
        ( D ) OTHER INFORMATION: /label=ATG
            / note= "translation initiation codon"

( x i ) SEQUENCE DESCRIPTION: SEQ ID NO:6:

CCATGGCACT AC                                                  12

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "region of MnSOD gene coding
            for region of SOD precursor protein around the transit
            peptide processing site"

( x i ) SEQUENCE DESCRIPTION: SEQ ID NO:7:

CTCCGCGGCT TGCAGACCTT TTCGCTC                            27

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "region of mutated MnSOD
            gene coding for region of SOD precursor protein around
            the transit peptide processing site"

( i x ) FEATURE:
        ( A ) NAME/KEY: -
        ( B ) LOCATION: 21..26
        ( D ) OTHER INFORMATION: /label=PstI
            / note= "recognition sequence for PstI introduced by
            site- directed mutagene..."

( x i ) SEQUENCE DESCRIPTION: SEQ ID NO:8:

CTCCGCGGCT TGCAGACCTT CTGCAGC                            27

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: protein ( i x ) FEATURE:
    ( A ) NAME/KEY: Region
    ( B ) LOCATION: 1..6
    ( D ) OTHER INFORMATION: /label=SOD
        / note= "N-terminal region of mature SOD"

( x i ) SEQUENCE DESCRIPTION: SEQ ID NO:9:

```
Leu  Gln  Thr  Phe  Ser  Leu
1                   5
```

( 2 ) INFORMATION FOR SEQ ID NO:10:

( i ) SEQUENCE CHARACTERISTICS:
        ( A ) LENGTH: 549 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Streptomyces hygroscopicus
        ( B ) STRAIN: ATCC 21705

( i x ) FEATURE:
        ( A ) NAME/KEY: -
        ( B ) LOCATION: 1..549
        ( D ) OTHER INFORMATION: /label=sfr
            / note= "region coding for phosphinothricin
            acetyltransferase (translation initiation codon GTG may
            be changed to ATG for use in plant cells)"

( i x ) FEATURE:
        ( A ) NAME/KEY: -
        ( B ) LOCATION: 1..3
        ( D ) OTHER INFORMATION: /label=GTG
            / note= "GTG may be changed to ATG for use in plants"

( x i ) SEQUENCE DESCRIPTION: SEQ ID NO:10:

```
GTGAGCCCAG  AACGACGCCC  GGCCGACATC  CGCCGTGCCA  CCGAGGCGGA  CATGCCGGCG    60
GTCTGCACCA  TCGTCAACCA  CTACATCGAG  ACAAGCACGG  TCAACTTCCG  TACCGAGCCG   120
CAGGAACCGC  AGGAGTGGAC  GGACGACCTC  GTCCGTCTGC  GGGAGCGCTA  TCCCTGGCTC   180
GTCGCCGAGG  TGGACGGCGA  GGTCGCCGGC  ATCGCCTACG  CGGGCCCCTG  GAAGGCACGC   240
AACGCCTACG  ACTGGACGGC  CGAGTCGACC  GTGTACGTCT  CCCCCCGCCA  CCAGCGGACG   300
GGACTGGGCT  CCACGCTCTA  CACCCACCTG  CTGAAGTCCC  TGGAGGCACA  GGGCTTCAAG   360
AGCGTGGTCG  CTGTCATCGG  GCTGCCCAAC  GACCCGAGCG  TGCGCATGCA  CGAGGCGCTC   420
GGATATGCCC  CCCGCGGCAT  GCTGCGGGCG  GCCGGCTTCA  AGCACGGGAA  CTGGCATGAC   480
GTGGGTTTCT  GGCAGCTGGA  CTTCAGCCTG  CCGGTACCGC  CCCGTCCGGT  CCTGCCCGTC   540
ACCGAGATC                                                                549
```

( 2 ) INFORMATION FOR SEQ ID NO:11:

( i ) SEQUENCE CHARACTERISTICS:
        ( A ) LENGTH: 183 amino acids
        ( B ) TYPE: amino acid
        ( C ) STRANDEDNESS:
        ( D ) TOPOLOGY: linear ( i i ) MOLECULE TYPE: protein ( v i ) ORIGINAL SOURCE:
        ( A ) ORGANISM: Streptomyces hygroscopicus
        ( B ) STRAIN: ATCC 21705

( i x ) FEATURE:

( A ) NAME/KEY: Region
( B ) LOCATION: 1..2
( D ) OTHER INFORMATION: /note= "Xaa may be Val or Met"

( i x ) FEATURE:
( A ) NAME/KEY: Protein
( B ) LOCATION: 1..183
( D ) OTHER INFORMATION: /label=PAT
/ note= "phosphinothricin acetyl transferase"

( x i ) SEQUENCE DESCRIPTION: SEQ ID NO:11:

```
Xaa  Ser  Pro  Glu  Arg  Arg  Pro  Ala  Asp  Ile  Arg  Arg  Ala  Thr  Glu  Ala
1               5                        10                       15

Asp  Met  Pro  Ala  Val  Cys  Thr  Ile  Val  Asn  His  Tyr  Ile  Glu  Thr  Ser
               20                       25                       30

Thr  Val  Asn  Phe  Arg  Thr  Glu  Pro  Gln  Glu  Pro  Gln  Glu  Trp  Thr  Asp
          35                       40                       45

Asp  Leu  Val  Arg  Leu  Arg  Glu  Arg  Tyr  Pro  Trp  Leu  Val  Ala  Glu  Val
     50                       55                       60

Asp  Gly  Glu  Val  Ala  Gly  Ile  Ala  Tyr  Ala  Gly  Pro  Trp  Lys  Ala  Arg
65                       70                       75                       80

Asn  Ala  Tyr  Asp  Trp  Thr  Ala  Glu  Ser  Thr  Val  Tyr  Val  Ser  Pro  Arg
               85                       90                       95

His  Gln  Arg  Thr  Gly  Leu  Gly  Ser  Thr  Leu  Tyr  Thr  His  Leu  Leu  Lys
               100                      105                      110

Ser  Leu  Glu  Ala  Gln  Gly  Phe  Lys  Ser  Val  Val  Ala  Val  Ile  Gly  Leu
               115                      120                      125

Pro  Asn  Asp  Pro  Ser  Val  Arg  Met  His  Glu  Ala  Leu  Gly  Tyr  Ala  Pro
     130                      135                      140

Arg  Gly  Met  Leu  Arg  Ala  Ala  Gly  Phe  Lys  His  Gly  Asn  Trp  His  Asp
145                      150                      155                      160

Val  Gly  Phe  Trp  Gln  Leu  Asp  Phe  Ser  Leu  Pro  Val  Pro  Pro  Arg  Pro
               165                      170                      175

Val  Leu  Pro  Val  Thr  Glu  Ile
               180
```

( 2 ) INFORMATION FOR SEQ ID NO:12:

( i ) SEQUENCE CHARACTERISTICS:
( A ) LENGTH: 618 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Streptomyces viridochromogenes
( B ) STRAIN: DSM 40736

( i x ) FEATURE:
( A ) NAME/KEY: -
( B ) LOCATION: 51..599
( D ) OTHER INFORMATION: /label=sfrsv
/ note= "region coding for phosphinothricin
acetyltransferase (GTG translation initiation codon may
be changed to ATG for use in plants)"

( x i ) SEQUENCE DESCRIPTION: SEQ ID NO:12:

```
TAAAGAGGTG CCCGCCACCC GCTTTCGCAG AACACCGAAG GAGACCACAC GTGAGCCCAG    60
AACGACGCCC GGTCGAGATC CGTCCCGCCA CCGCCGCCGA CATGGCGGCG TCTGCGACA    120
TCGTCAATCA CTACATCGAG ACGAGCACGG TCAACTTCCG TACGGAGCCG CAGACTCCGC   180
AGGAGTGGAT CGACGACCTG GAGCGCCTCC AGGACCGCTA CCCCTGGCTC GTCGCCGAGG   240
```

-continued

```
TGGAGGGCGT CGTCGCCGGC ATCGCCTACG CCGGCCCCTG GAAGGCCCGC AACGCCTACG      300

ACTGGACCGT CGAGTCGACG GTGTACGTCT CCCACCGGCA CCAGCGGCTC GGACTGGGCT      360

CCACCCTCTA CACCCACCTG CTGAAGTCCA TGGAGGCCCA GGGCTTCAAG AGCGTGGTCG      420

CCGTCATCGG ACTGCCCAAC GACCCGAGCG TGCGCCTGCA CGAGGCGCTC GGATACACCG      480

CGCGCGGGAC GCTGCGGGCA GCCGGCTACA AGCACGGGGG CTGGCACGAC GTGGGGTTCT      540

GGCAGCGCGA CTTCGAGCTG CCGGCCCCGC CCCGCCCCGT CCGGCCCGTC ACACAGATCT      600

GAGCGGAGAG CGCATGGC                                                    618
```

(2) INFORMATION FOR SEQ ID NO:13:

(i) SEQUENCE CHARACTERISTICS:
        (A) LENGTH: 183 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Streptomyces viridochromogenes
        (B) STRAIN: DSM 40736

(ix) FEATURE:
        (A) NAME/KEY: Region
        (B) LOCATION: 1..2
        (D) OTHER INFORMATION: /note= "may be changed to Met for
            use in plants"

(ix) FEATURE:
        (A) NAME/KEY: Protein
        (B) LOCATION: 1..183
        (D) OTHER INFORMATION: /label=PAT
            / note= "phosphinothricin acetyl transferase"

(xi) SEQUENCE DESCRIPTION: SEQ ID NO:13:

```
Val Ser Pro Glu Arg Arg Pro Val Glu Ile Arg Pro Ala Thr Ala Ala
 1               5                  10                  15

Asp Met Ala Ala Val Cys Asp Ile Val Asn His Tyr Ile Glu Thr Ser
             20                  25                  30

Thr Val Asn Phe Arg Thr Glu Pro Gln Thr Pro Gln Glu Trp Ile Asp
         35                  40                  45

Asp Leu Glu Arg Leu Gln Asp Arg Tyr Pro Trp Leu Val Ala Glu Val
     50                  55                  60

Glu Gly Val Val Ala Gly Ile Ala Tyr Ala Gly Pro Trp Lys Ala Arg
 65                  70                  75                  80

Asn Ala Tyr Asp Trp Thr Val Glu Ser Thr Val Tyr Val Ser His Arg
                 85                  90                  95

His Gln Arg Leu Gly Leu Gly Ser Thr Leu Tyr Thr His Leu Leu Lys
            100                 105                 110

Ser Met Glu Ala Gln Gly Phe Lys Ser Val Val Ala Val Ile Gly Leu
        115                 120                 125

Pro Asn Asp Pro Ser Val Arg Leu His Glu Ala Leu Gly Tyr Thr Ala
    130                 135                 140

Arg Gly Thr Leu Arg Ala Ala Gly Tyr Lys His Gly Gly Trp His Asp
145                 150                 155                 160

Val Gly Phe Trp Gln Arg Asp Phe Glu Leu Pro Ala Pro Pro Arg Pro
                165                 170                 175

Val Arg Pro Val Thr Gln Ile
            180
```